US012638440B2

(12) United States Patent
Ozbolat et al.

(10) Patent No.: US 12,638,440 B2
(45) Date of Patent: May 26, 2026

(54) ORGAN MODELS

(71) Applicant: The Penn State Research Foundation, University Park, PA (US)

(72) Inventors: Ibrahim Tarik Ozbolat, Boalsburg, PA (US); Monika Hospodiuk, State College, PA (US); Dino Joseph Ravnic, Hershey, PA (US); Bugra Ayan, State College, PA (US); Srinivas Koduru, Mechanicsburg, PA (US)

(73) Assignee: The Penn State Research Foundation, University Park, PA (US)

( * ) Notice: Subject to any disclaimer, the term of this patent is extended or adjusted under 35 U.S.C. 154(b) by 233 days.

(21) Appl. No.: 17/827,357

(22) Filed: May 27, 2022

(65) Prior Publication Data

US 2022/0291201 A1     Sep. 15, 2022

Related U.S. Application Data

(62) Division of application No. 16/477,067, filed as application No. PCT/US2018/013590 on Jan. 12, 2018, now abandoned.

(60) Provisional application No. 62/515,850, filed on Jun. 6, 2017, provisional application No. 62/445,932, filed on Jan. 13, 2017.

(51) Int. Cl.
| | |
|---|---|
| *C12N 5/071* | (2010.01) |
| *G01N 33/50* | (2006.01) |
| *C12M 1/00* | (2006.01) |
| *C12M 1/12* | (2006.01) |
| *C12M 3/06* | (2006.01) |

(52) U.S. Cl.
CPC ......... *G01N 33/507* (2013.01); *C12N 5/0676* (2013.01); *C12M 23/16* (2013.01); *C12M 25/14* (2013.01); *C12M 29/10* (2013.01); *G01N 33/5064* (2013.01)

(58) Field of Classification Search
None
See application file for complete search history.

(56) References Cited

U.S. PATENT DOCUMENTS

| | | | |
|---|---|---|---|
| 2002/0142458 A1 | 10/2002 | Williams et al. | |
| 2002/0182241 A1* | 12/2002 | Borenstein | C12M 21/08 |
| | | | 428/188 |
| 2013/0029875 A1* | 1/2013 | Stehno-Bittel | C12M 23/12 |
| | | | 435/395 |
| 2015/0217024 A1 | 8/2015 | Wang et al. | |
| 2016/0287756 A1* | 10/2016 | Lewis | B33Y 10/00 |
| 2017/0009194 A1 | 1/2017 | Golway et al. | |
| 2018/0030409 A1 | 2/2018 | Lewis et al. | |
| 2019/0331662 A1 | 10/2019 | Ozbolat et al. | |

OTHER PUBLICATIONS

Ning, Liqun, and Xiongbiao Chen. "A brief review of extrusion-based tissue scaffold bio-printing." Biotechnology journal 12.8 (May 24, 2017): 1600671. (Year: 2017).*

Lee et al. "In situ formation and collagen-alginate composite encapsulation of pancreatic islet spheroids." Biomaterials 33.3 (2012): 837-845 (Year: 2012).*

Atkinson et al., "Type 1 diabetes," Lancet, 383(9911):69-82, Jan. 2014.

Boldison et al., "Immune and Pancreatic β Cell Interactions in Type 1 Diabetes," Trends Endocrinol. Metab., 27(12):856-67, Dec. 2016.

Faglia et al., "Early and Five-year Amputation and Survival Rate of Diabetic Patients with Critical Limb Ischemia: Data of a Cohort Study of 564 Patients," Eur. J. Vasc. Endovasc. Surg., 32(5):484-90, Nov. 2006.

Fava et al., "Novel standards in the measurement of rat insulin granules combining electron microscopy, high-content image analysis and in silico modelling," Diabetologia, 55(4):1013-23, Apr. 2012.

Forbes and Cooper, "Mechanisms of diabetic complications," Physiological reviews, 93(1):137-88, Jan. 2013.

Jun et al., "Microfluidics-generated pancreatic islet microfibers for enhanced immunoprotection," Biomaterials 34(33):8122-30, Aug. 2013.

King et al., "The use of animal models in diabetes research," Br. J. Pharmacol., 166(3):877-94, Feb. 2012.

Leksell et al., "Sense of coherence and power among people with blindness caused by diabetes," Diabetes Res. Clin. Pract., 67(2):124-9, Feb. 2005.

MedlinePlus.gov[online] "Islet Cell Transplantation," available on or before Dec. 21, 2016 via Internet Archive: Wayback Machine URL <https://web.archive.org/web/20161221183007/https://medlineplus.gov/isletcelltransplantation.html>, 3 pages, retrieved on Aug. 29, 2019.

Migliorini et al., "Islet cell plasticity and regeneration," Mol. Metab., 3(3):268-74, Jun. 2014.

Milliam et al., "Generation of Stem Cell-Derived β-Cells From Patients With Type 1 Diabetes," Nat. Commun., 7:11463, May 2016.

Napolitano et al., "Scaffold-free three-dimensional cell culture utilizing micromolded nonadhesive hydrogels," Biotechniques, 43(4):494-500, Oct. 2007.

Ozbolat et al., "Application areas of 3D bioprinting," Drug Discov. Today, 21(8):1257-71, Aug. 2016.

Pagiluca et al., "Generation of functional human pacreatic β cells in vitro," Cell, 159:428-39, Oct. 2014.

Pagiluca et al., "How to make a functional β-cell," Development, 140:2472-83, Jun. 2013.

PCT International Preliminary Report on Patentability in International Appln. No. PCT/US2018/013590 dated Jul. 25, 2019, 10 pages.

PCT International Search Report and Written Opinion in International Appln. No. PCT/US2018/013590 dated Apr. 4, 2018, 11 pages.

(Continued)

*Primary Examiner* — Emily A Cordas
(74) *Attorney, Agent, or Firm* — Fish & Richardson P.C.

(57) ABSTRACT

This document provides materials and methods for making and using functional (e.g., vascularized) organ models (e.g., pancreas models). For example, functional pancreas models including an ECM containing a plurality (e.g., two or more) of pancreatic islets, and a vascular network are provided.

20 Claims, 15 Drawing Sheets

(56)                    References Cited

OTHER PUBLICATIONS

Peng et al., "Bioprinting towards Physiologically Relevant Tissue Models for Pharmaceutics," Trends Biotechnol., 34(9):722-32, Sep. 2016.

Piran et al., "Pharmacological induction of pancreatic islet cell transdifferentiation: relevance to type I diabetes." Cell Death Dis., 5:e1357, Jul. 2014.

Van Herrath et al., "Animal models of human type 1 diabetes" Nat. Immunol., 10(2):129-32, Feb. 2009.

Vivo.com [online] "Functional Anatomy of the Endocrine Pancreas" available on or before Dec. 21, 2016, via Internet Archive: Wayback Machine URL <https://web.archive.org/web/20161221201856/http://www.vivo.colostate.edu/hbooks/pathphys/endocrine/pancreas/anatomy.html>, retrieved on Aug. 29, 2019, 2 pages.

Yu et al., "Three-dimensional bioprinting using self-assembling scalable scaffold-free "tissue strands" as a new bioink," Sci. Rep., 6:28714, Jun. 2016.

Zhu et al., "Human pancreatic beta-like cells converted from Fibroblasts", Nat. Comm., 7:10080, Jan. 2016.

* cited by examiner

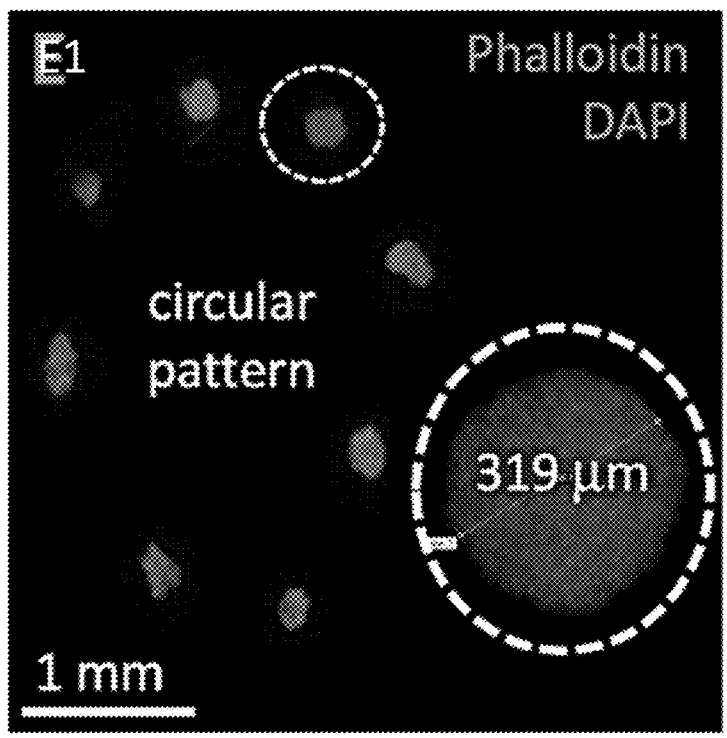
FIG. 9E1
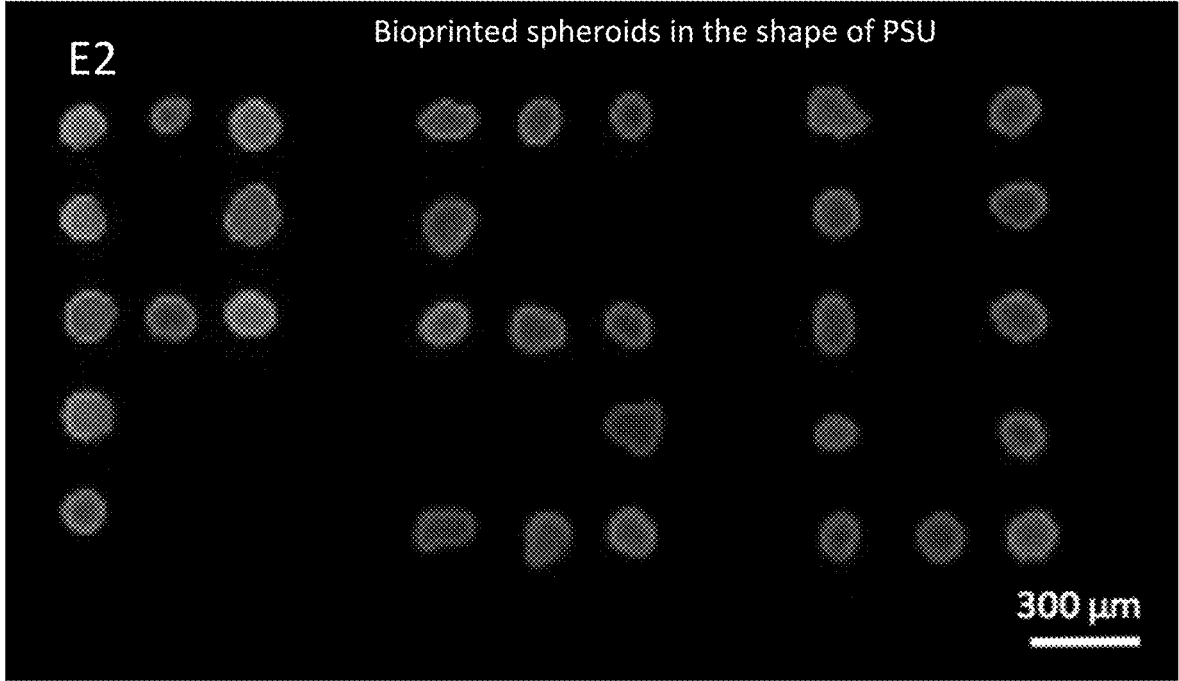
FIG. 9E2

ORGAN MODELS

CROSS-REFERENCE TO RELATED APPLICATIONS

This application is a Divisional Application of U.S. patent application Ser. No. 16/477,067, filed Jul. 10, 2019, which is a National Stage application under 35 U.S.C. § 371 of International Application No. PCT/US2018/013590, having an International Filing Date of Jan. 12, 2018, which claims the benefit of U.S. Patent Application Ser. No. 62/445,932, filed on Jan. 13, 2017, and U.S. Patent Application Ser. No. 62/515,850, filed on Jun. 6, 2017. The disclosures of the prior applications are considered part of (and are incorporated by reference in) the disclosure of this application.

STATEMENT REGARDING FEDERAL FUNDING

This invention was made with government support under Grant No. CMMI1624515, awarded by the National Science Foundation. The Government has certain rights in the invention.

BACKGROUND

1. Technical Field

This document relates to materials and methods for making and using functional (e.g., vascularized and/or innervated) organ models (e.g., pancreas models and tumor models). For example, functional pancreas models provided herein can be designed to include an extracellular matrix (ECM) containing a plurality (e.g., two or more) of pancreatic islets, and a vascular network.

2. Background Information

Type-1 diabetes (TID) is a devastating disease caused by malfunction or complete loss of insulin production by beta (β)-cells in islets of Langerhans in the pancreas (Atkinson et al., *Lancet,* 383:69-82 (2014)). As a result, insulin is produced minimally or not at all. In most cases, T1D is caused by an autoimmune response, whereby the immune system attacks β-cells and destroys them. It is a chronic disease that often leads to severe complications including blindness, limb amputations, kidney failure, neuropathy, and cardiovascular diseases (Faglia et al., *Eur. J. Vasc. Endovasc. Surg.,* 32:484-490 (2006); Leksell et al., *Diabetes Res. Clin. Pract.,* 67:124-129 (2005); and Forbes et al., *Physiol. Rev.,* 93:137-88 (2013)). Until now, T1D has been managed by subcutaneous insulin injections and cure has been attempted by the transplantation of cadaveric pancreases or islets (Migliorini et al., *Mol. Metab.,* 3:268-74 (2014)).

SUMMARY

Current pancreas models used in drug testing are limited to mouse models (King et al., *Br J Pharmacol* 166:877-94 (2012); and van Herrath et al., *Nat Immunol* 10:129-32 (2009)), which do not fully represent the complex biology of their human counterparts (Peng et al., 2016 *Trends Biotechnol.* 34:722-32). The scarcity of human islets and the limited viability of human β cells ex vivo (Migliorini et al., *Mol Metab* 3:268-74 (2014)) necessitate alternative solutions for models of human pancreas to study immune cell-beta cell interactions in type 1 diabetes (Boldison et al., *Trends*

*Endocrinol Metab.* 27:856-867 (2016)) as well as the pharmacology of the endocrine pancreas (Peng et al., *Trends Biotechnol.* 34:722-32 (2016 0; and Piran et al., *Cell Death Dis* 5:e1357 (2014)).

This document relates to materials and methods for making and using functional (e.g., vascularized) organ models (e.g., pancreas models). For example, functional pancreas models provided herein can be designed to include an ECM containing a plurality (e.g., two or more) of pancreatic islets, and a vascular network. In some cases, a functional pancreas model provided herein can be used in vitro to study the biology (e.g., multicellular interactions) of the human pancreas and/or to evaluate therapeutic agents.

As demonstrated herein, β-cell clusters in a three-dimensional (3D) hydrogel culture can be engineered into pancreatic islets with vascularization. For example, murine pancreatic beta cell line (e.g., β-TC3 cells) and rat heart microvessel endothelial cells (MVECs) can be grown in clusters in a fibrin hydrogel and vascularized to create engineered pancreatic spheroids (EPSs). Also as demonstrated herein, functional adipocyte-derived stem cell (ADSC)-derived β-cells can be generated and used to bioprint (e.g., 3D bioprint) a functional (e.g., vascularized) pancreas tissue that mimics the physiology and architecture of a human endocrine pancreas.

Having the ability to generate a functional human pancreas provides a model that recapitulates the physiology and/or architecture of a human pancreas and provides a unique and unrealized opportunity to evaluate the effect of various therapeutic agents (e.g., T1D drugs) on the human pancreas (e.g., without requiring human testing).

In general, one aspect of this document features a device capable of being used as a pancreas model. A device can include a substrate, a lower layer of ECM disposed on top of the substrate, a strand of matrix (e.g., sacrificial matrix) disposed along an interior region of the lower layer of ECM, an array of pancreatic islets disposed on top of the lower layer of ECM, an upper layer of ECM disposed on the array of pancreatic islets, and a vascular network. The lower layer of ECM can include fibrin, thrombin, fibrinogen, fibrin hydrogel, collagen (e.g., collagen type IV), gelatin, a gelatinous protein mixture (e.g., Matrigel®), and/or laminin. The lower layer of ECM can include endothelial cells, pericytes, fibroblasts, smooth muscle cells, or combinations thereof. The lower layer of ECM can include calcium chloride ($CaCl_2$). The matrix (e.g., sacrificial matrix) can be alginate, agarose, gelatin, sugar, and/or poloxamer (e.g., Pluronic® such as Pluronic® F-127). The pancreatic islets can include β cells and MVECs. The β cells can include ADSC-derived β cells, induced pluripotent stem cell (IPS) derived beta cells, fibroblast derived beta cells, or any combination thereof. The 3 cells and the MVECs can be present in a ratio of from about 1:1 to about 10:1. The upper layer of ECM can include fibrin, thrombin, fibrinogen, fibrin hydrogel, collagen (e.g., collagen type IV), gelatin, a gelatinous protein mixture (e.g., Matrigel®), and/or laminin. The upper layer of ECM can include endothelial cells, pericytes, fibroblasts, smooth muscle cells, or combinations thereof. The upper layer of ECM can include $CaCl_2$).

In another aspect, this document features a method for making a pancreas model. The method can include, or consist essentially of, disposing a first layer of ECM onto a substrate assembled into a model platform, disposing a strand of matrix (e.g., sacrificial matrix) onto an interior region of the first layer of ECM, disposing an array of pancreatic islets onto the first layer of ECM, disposing a layer of ECM onto the array of pancreatic islets, de-crosslinking the matrix (e.g., sacrificial matrix) with a solution to create a channel, seeding the channel with ECs, and perfusing the channel with perfusate.

Disposing the first layer of ECM can include alternately disposing a first layer including thrombin, ECs, pericytes, and $CaCl_2$, and disposing a second layer including fibrinogen on the first layer. The matrix (e.g., sacrificial matrix) can be alginate, agarose, gelatin, sugar, or poloxamer (e.g., Pluronic® such as Pluronic® F-127). The pancreatic islets can be EPSs. The EPSs can be engineered by co-culturing β cells and MVECs. The β cells can include ADSC-derived β cells, pluripotent stem cell derived beta cells, fibroblast derived beta cells, or any combination thereof. The β cells and the MVECs can be co-cultured in a ratio of from about 1:1 to about 10:1. The β cells and the MVECs can be co-cultured in the presence of a growth factor (e.g., vascular endothelial growth factor, epidermal growth factor, and fibroblast growth factor). Disposing the second layer of ECM can include alternately disposing a first layer including thrombin, ECs, pericytes, and $CaCl_2$, and disposing a second layer including fibrinogen on the first layer until the model platform is full. The solution can be sodium citrate. The channel can be perfused with laminar flow. The channel can be perfused for about 14 days at a rate of about 0.1 dyne/cm$^2$ for about 6 hours, followed by a rate of about 1 dyne/cm$^2$ for about 18 hours, followed by a rate of about 10 dyne/cm$^2$ for about 13 days. The perfusate can be serum-free media. The pancreas model can be a patient-specific pancreas model.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figures 1A, 1B:
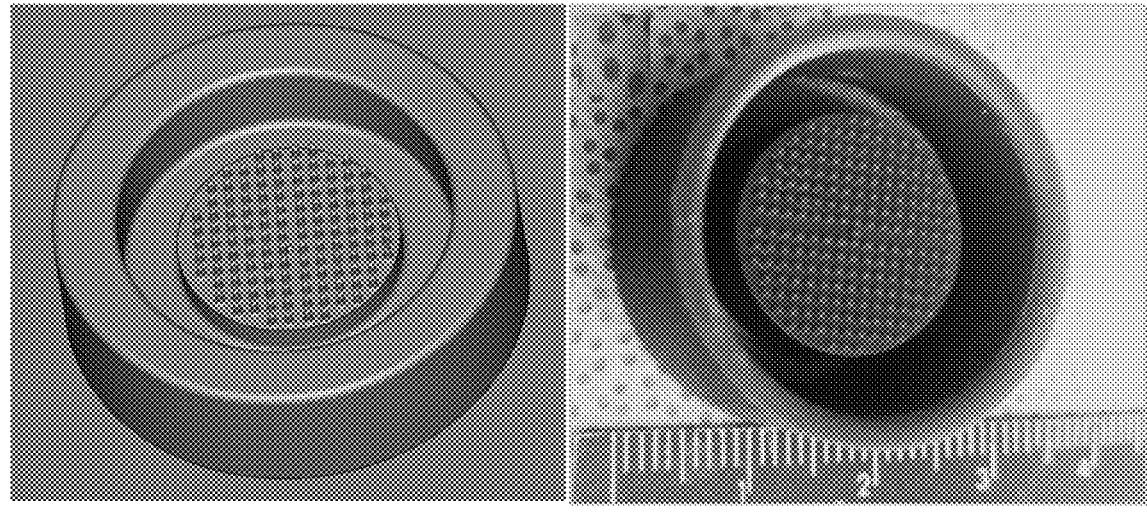
FIG. 1 shows a schematic (A) and a photograph (B) of 3D printed agarose molds.

This document provides materials and methods for making and using functional (e.g., vascularized) organ models (e.g., pancreas models). For example, functional pancreas models provided herein can be designed to include an ECM containing a plurality (e.g., two or more) of pancreatic islets, and a vascular network. In some cases, a vascularized human pancreas model can be used in vitro to study the biology of the human pancreas and/or to evaluate therapeutic agents.

Organ Models

Functional organ models provided herein (e.g., human pancreas models and human tumor models) can recapitulate the physiology and/or architecture of an organ (e.g., a pancreas). For example, a pancreas model provided herein can include an ECM containing a plurality (e.g., two or more) of vascularized islets connected by one or more anastomoses. For example, a pancreas model provided herein can include a plurality (e.g., two or more) nerves. In some cases, a pancreas model can include a lower layer of ECM, a plurality of pancreatic islets connected by a vascular network, and an upper layer of ECM. Organ models provided herein can be 3D organ models. In some cases, an organ model provided herein can be a functional (e.g., vascularized and/or innervated) organ model.

An organ model provided herein can be a model of any appropriate organ (e.g., pancreas, skin, heart, liver, kidney, and lung). In some cases, an organ model provided herein is a pancreas model.

An organ model provided herein can be a tumor model. A tumor model can be a model of any appropriate cancer type (e.g., pancreatic cancer, breast cancer, lung cancer, prostate cancer, ovarian cancer, and melanoma). In some cases, a tumor model provided herein is a breast cancer model.

An organ model provided herein can be a model of an organ from any appropriate mammal (e.g., a human, mouse, rat, dog, and cat). In some cases, an organ model provided herein is a human organ model.

In some cases, organ models provided herein (e.g., human pancreas models and human tumor models) can include (e.g., be on and/or within) a device (e.g., a model platform). Organ models present on and/or within a model platform can also be referred to an organ-on-a-chip (e.g., a pancreas-on-a-chip) model. A model platform can be made of any appropriate material. Examples of materials that can be used for a model platform include, without limitation, glass, plastic (e.g., polystyrene), and rubber (e.g., silicone). A material used for a model platform can be a sterile material. A material used for a model platform can be a biocompatible material. A platform can include an opening such that a liquid (e.g., a perfusate) can be perfused through the model platform. In some cases, a model platform can have two-parts (e.g., having a bottom portion and an upper portion). A bottom portion of a model platform can include a bottom face. In some cases, a bottom face of a bottom portion of a model platform can be a different material from the rest of the device. For example, a bottom face can be optically transparent (e.g., to facilitate imaging). In some cases, a model platform can include a well (e.g., in a multiwell plate). In some cases, a model platform can include a substrate (e.g., a chip such as a microfluidics chip). In cases where the model platform has a bottom portion and an upper portion, the upper portion can provide outer walls (e.g., within which organ models provided herein (e.g., pancreas models) can be contained) and can be open on its top and bottom surfaces. In some cases, an upper portion that is open on its top can have the opening sealed (e.g., to aid in maintaining sterile conditions) with, for example, glass (e.g., a glass coverslip). In cases where the model platform has two-parts, the two-parts can be assembled using a press-fit assembly.

Organ models provided herein (e.g., functional, 3D, human pancreas models) can be any appropriate size. In some cases, an organ model can have a width of about 0.5 mm to about 5 mm (e.g., about 0.8 mm to about 5 mm, about 1.0 mm to about 5 mm, about 1.3 mm to about 5 mm, about 1.5 mm to about 5 mm, about 1.8 mm to about 5 mm, about 2.0 mm to about 5 mm, about 2.5 mm to about 5 mm, about 0.5 mm to about 4.5 mm, about 0.5 mm to about 4.2 mm, about 0.5 mm to about 4.0 mm, about 0.5 mm to about 3.8 mm, about 0.5 mm to about 3.5 mm, or about 0.5 mm to about 3.0 mm). In some cases, an organ model can have a depth of about 0.5 mm to about 10 mm (e.g., about 1 mm to about 10 mm, about 2 mm to about 10 mm, about 3 mm to about 10 mm, about 4 mm to about 10 mm, about 5 mm to about 10 mm, about 6 mm to about 10 mm, about 0.5 mm to about 9 mm, about 0.5 mm to about 8 mm, about 0.5 mm to about 7 mm, about 0.5 mm to about 6 mm, about 0.5 mm to about 5 mm, about 1 mm to about 8 mm, about 3 mm to about 7 mm, or about 4 mm to about 6 mm). In some cases, an organ model can have a height of about 0.5 mm to about 1 mm (e.g., about 0.5 mm to about 0.9 mm, about 0.5 mm to about 0.8 mm, about 0.5 mm to about 0.7 mm, about 0.5 mm to about 0.6 mm, about 0.6 mm to about 1 mm, about 0.7 mm to about 1 mm, about 0.8 mm to about 1 mm, or about 0.9 mm to about 1 mm). For example, an organ model can be from about 0.5 mm×0.5 mm×0.5 mm to about 5×10 mm×1 mm in size (e.g., width×depth×height).

In cases where an organ model is a pancreas model, the pancreas model can include any appropriate number of pancreatic islets (e.g., EPSs). For example, a pancreas model provided herein can include between about 20 islets per $mm^3$ and about 50 islets per $mm^3$ (e.g., between about 25 islets per $mm^3$ and about 50 islets per $mm^3$, between about 30 islets per $mm^3$ and about 50 islets per $mm^3$, between about 35 islets per $mm^3$ and about 50 islets per $mm^3$, between about 40 islets per $mm^3$ and about 50 islets per $mm^3$, between about 20 islets per $mm^3$ and about 45 islets per $mm^3$, between about 20 islets per $mm^3$ and about 40 islets per $mm^3$, between about 20 islets per $mm^3$ and about 35 islets per $mm^3$, or between about 20 islets per $mm^3$ and about 30 islets per $mm^3$). An islet can be any appropriate size. In some cases, an islet can have a longest diameter from about 50 μm to about 330 μm (e.g., from about 50 μm to about 300 μm, from about 50 μm to about 250 μm, from about 50 μm to about 200 μm, from about 50 μm to about 150 μm, from about 50 μm to about 100 μm, from about 50 μm to about 75 μm, from about 75 μm to about 330 μm, from about 100 μm to about 330 μm, from about 150 μm to about 330 μm, from about 200 μm to about 330 μm, from about 250 μm to about 330 μm, from about 300 μm to about 330 μm, from about 175 μm to about 320 μm, from about 200 μm to about 300 μm, from about 200 μm to about 290 μm, from about 200 μm to about 275 μm, from about 200 μm to about 260 μm, from about 200 μm to about 250 μm, from about 200 μm to about 225 μm, from about 210 μm to about 300 μm, from about 225 μm to about 300 μm, from about 230 μm to about 300

μm, from about 240 μm to about 300 μm, from about 250 μm to about 300 μm, or from about 260 μm to about 300 μm).

An organ model provided herein (e.g., a functional, 3D, human pancreas model) can be vascularized. For example, in cases where an organ model is a pancreas model having a plurality (e.g., two or more) of islets (e.g., EPSs), the islets can include vascularization (e.g., neovascularization) within the islets. For example, in cases where an organ model is a pancreas model having a plurality of islets, the islets can be connected by one or more anastomoses (e.g., connections between blood vessels; also referred to as a vascular network). A vascular network can be a microvascular network or a macrovascular network.

In some cases, organ models provided herein (e.g., a functional, 3D, human pancreas model) can be stable (e.g., can maintain organ physiology and architecture). For example, an organ model can be viable and/or perfusable while on a model platform. In cases where an organ model is a pancreas model, the pancreas model can be perfusable in the device for at least about 5 (e.g., at least about 7, at least about 8, at least about 10, at least about 12, at least about 15, at least about 18, at least about 20, at least about 21, at least about 22, at least about 23, at least about 24, at least about 25, or at least about 26) days. In cases where an organ model is a pancreas model, the pancreas model can be perfusable in the device for at least about 1 month (e.g., at least about 2, at least about 3, at least about 4, at least about 5, or at least about 6 months).

In some cases, an organ model provided herein (e.g., a functional, 3D, human pancreas model) can be a heterocellular organ model. For example, a heterocellular organ model can include multiple (e.g., two or more) different cell types, cell tissues, and/or organoids. In cases where an organ model is a pancreas model, the pancreas model can include an ECM, a plurality of islets (e.g., EPSs), and a vascular network.

Method of Making Organ Models

This document provides methods for making organ models described herein (e.g., human pancreas models and human tumor models). In some cases, organ models provided here are fabricated by accurate disposing of biomaterials (e.g., cells, organoids, ECM components, growth factors, signaling molecules, genes, nanoparticles, cytokines, and/or other functional components) on a model platform to recapitulate the native physiology and/or architecture of an organ. For example, pancreas models can be fabricated by disposing pancreatic biomaterials on a model platform to form a lower layer of ECM, one or more open lumens (e.g., one or more channels), an array of organoids (e.g., pancreatic islets), and an upper layer of ECM, and perfusing the disposed biomaterials under conditions where the biomaterials self-assemble to form a pancreas model having a vascular network. In some cases, fabricating a 3D organ model can include depositing biomaterials on a device (e.g., a model platform) described herein. For example, biomaterials deposited on a model platform can self-assemble to form an organ model. In some cases, organ models can be fabricated without the use of a scaffold.

An ECM in pancreas models can include any appropriate biomaterials (e.g., pancreatic biomaterials). In cases where pancreatic biomaterials include cells, the cells can include any appropriate cells. In some cases, cells used to fabricate organ models described herein can be endothelial cells (ECs). Examples of ECs that can be used when making an organ model provided herein include, without limitation, BMECs, and MVEC. In some cases, cells used to fabricate organ models described herein can be stromal cells (e.g., supporting stromal cells). Examples of stromal cells that can be used when making an organ model provided herein include, without limitation, pericytes, fibroblasts, and smooth muscle cells. Cells can be obtained from any appropriate mammal (e.g., a human, mouse, rat, dog, and cat). In some cases, cells can be human cells. In cases where pancreatic biomaterials include ECM components, the ECM components can include any appropriate ECM components. Examples of ECM components that can be used to make an organ model provided herein include, without limitation, thrombin, fibrinogen, fibrin, fibrin hydrogel, collagen (e.g., collagen type IV), gelatin, a gelatinous protein mixture (e.g., Matrigel®), and laminin. In some cases, ECM components can be produced by cells used to fabricate organ models described herein (e.g., ECs such as MVECs). In cases where pancreatic biomaterials include other functional components, the other function materials can include any appropriate functional components. Examples of functional components that can be used to make an organ model provided herein include, without limitation, $CaCl_2$). In some cases, an ECM also can include one or more additional components. For example, an ECM also can include supporting stromal cells and/or supporting stromal tissues.

An ECM in pancreas models can be fabricated by disposing biomaterials, (e.g., pancreatic biomaterials) on a model platform in one or more layers. In some cases, a biomaterial layer can include multiple (e.g., 2, 3, 4, 5, 6, or more) biomaterials. For example, a biomaterial layer can include thrombin, ECs, stromal cells (e.g., pericytes), and $CaCl_2$. In some cases, a biomaterial layer can include a single biomaterial. For example, a biomaterial layer can include fibrinogen. In some cases, ECM can be fabricated by alternately disposing a first biomaterial layer including thrombin, ECs, pericytes, and $CaCl_2$), and a second biomaterial layer including fibrinogen. These alternating layers can be repeated any appropriate number of times (e.g., up to about 14 layers). For example, layers can be alternated until a model platform (e.g., a bottom portion and/or an upper portion of a model platform) is filled.

An array of organoids (e.g., pancreatic islets) in pancreas models can include any appropriate organoids. An array of pancreatic islets can include any appropriate number of pancreatic islets (e.g., between about 20 islets per $mm^3$ and about 50 islets per $mm^3$). An array of pancreatic islets can include pancreatic islets in any appropriate geometric arrangement (e.g., a pattern such as a ring-shaped pattern). In some cases, pancreatic islets used herein can be engineered pancreatic islets. For example, an engineered pancreatic islet can be an EPS. An EPS can be made using any appropriate technique. For example, β cells (e.g., ADSC-derived β-cells) and ECs (e.g., MVECs) can be co-cultured (e.g., 3D co-cultured) under angiogenic conditions (e.g., in the presence of one or more growth factors such as vascular endothelial growth factor (VEGF), epidermal growth factor (EGF), and/or fibroblast growth factor (FGF)) to form EPSs. In some cases, β cells (e.g., ADSC-derived β-cells) and ECs (e.g., MVECs) can be co-cultured in a ratio of β cells to ECs of about 1:1 to about 10:1 (e.g., about 1.5:1 to about 10:1, about 2:1 to about 10:1, about 3:1 to about 10:1, about 4:1 to about 10:1, about 5:1 to about 10:1, about 6:1 to about 10:1, about 7:1 to about 10:1, about 8:1 to about 10:1, about 9:1 to about 10:1, about 1:1 to about 9:1, about 1:1 to about 8:1, about 1:1 to about 7:1, about 1:1 to about 6:1, about 1:1 to about 5:1, about 1:1 to about 4:1, about 1:1 to about 3:1, about 1:1 to about 2:1, about 2:1 to about 9:1, about 3:1 to about 8:1, about 4:1 to about 7:1, about 5:1 to about 6:1, about 1.1:1 to about 2:1, about 1.3:1 to about 2:1, about 1.5:1 to about 2:1, about 1:1 to about 1.9:1, about 1:1 to about 1.7:1, or about 1:1 to about 1.5:1). The β cells and ECs can be obtained from any appropriate mammal (e.g., a human, mouse, rat, dog, and cat). The R cells can be derived from any appropriate cell. In some cases, β cells can be ADSC-derived β-cells. ADSC-derived R-cells can be obtained as described, for example, in the Examples. In some cases, β cells can be IPS-derived β cells. IPS-derived β cells can be obtained as described elsewhere (see, e.g., Pagliuca et al., 2014 *Cell* 158:428-439; and Millman et al., 2016 *Nat. Comm.* 7:11463). In some cases, β cells can be fibroblast-derived β cells. Fibroblast-derived β cells can be obtained as described elsewhere (see, e.g., Zhu et al., 2016 *Nat. Comm.* 7:10080). In some cases, derived β-cells can be derived from human cells. For example, ADSC-derived β-cells can be human ADSC-derived β-cells. In some cases, an organoid can be a vascularized organoid (e.g., a pre-vascularized organoid such as a pre-vascularized islet). In some cases, an organoid (e.g., an EPS) also can include one or more additional types of cells. For example, an EPS also can include α-cells, δ-cells, γ cells, ε-cells, and/or ECs.

An open lumen (e.g., a channel) in pancreas models can be made using any appropriate method. In some cases, one or more strands of temporary support material (e.g., a matrix such as a sacrificial matrix) can be disposed on a layer of ECM. The one or more strands of temporary support material can be disposed on a layer of ECM in any appropriate shape and/or pattern (e.g., a line or a network). For example, a strand of temporary support material can be disposed on a first layer (e.g., a lower layer) of ECM, and a second layer (e.g., an upper layer) of ECM can be disposed on the strand of temporary support material. A temporary support material can be any material that can be removed such that an open lumen is left in its place. In some cases, a strand of temporary support material can be disposed along a middle region of a first layer of ECM, and a second layer of ECM can be disposed on the strand of temporary support material such that the open lumen runs through the center of the pancreas model and is surrounded (e.g., completely surrounded) by ECM. Examples of materials that can be used as a temporary support (e.g., a sacrificial matrix) when making an organ model provided herein include, without limitation, alginate, agarose, gelatin, sugar, and poloxamer (e.g., Pluronic® such as Pluronic® F-127). The one or more strands of temporary support material can be any appropriate size. In some cases, the size of the one or more strands of temporary support material can reflect the diameter(s) (e.g., internal diameter(s)) of blood vessels in a vascular network. For example, an alginate strand can have a width of from about 200 μm to about 800 μm (e.g., from about 300 μm to about 800 μm, from about 400 μm to about 800 μm, from about 500 μm to about 800 μm, from about 600 m to about 800 μm, from about 200 m to about 700 μm, from about 200 μm to about 600 μm, from about 200 μm to about 500 μm, from about 200 μm to about 400 μm, from about 300 μm to about 700 μm or from about 400 μm to about 500 μm). In some cases, an alginate strand can have a width of from about 400 μm to about 500 μm. Strands of temporary support material can be removed using any appropriate method. For example, strands of temporary support material can be removed using a manual removal process or an aspiration removal process. In cases where the temporary support material is alginate, the alginate can be removed using a solution (e.g., sodium citrate) to decrosslink the alginate strand. For example, an organ model having one or more strands of alginate can be maintained in a sodium citrate solution to decrosslink the alginate strands. Removal of the one or more strands of temporary support material can be used to generate open lumens (e.g., of the same diameter(s) as the one or more alginate strands) within the organ model. In some cases, methods of removing alginate strands can be performed as described elsewhere (see, e.g., Yu et al., *Scientific Reports,* 6:28714 (2016)).

Vascular networks in pancreas models can be made using any appropriate method. In some cases, ECs (e.g., MVECs) can be seeded in an open lumen of a pancreas model, and the pancreas model can be perfused (e.g., under conditions where the biomaterials self-assemble to establish a vascular network). A pancreas model can be perfused with any appropriate perfusate (e.g., media such as serum-free media). A pancreas model can be perfused with any appropriate technique (e.g., laminar flow). A pancreas model can be perfused for any appropriate amount of time. For example, an organ model can be perfused for about 3 days to about 60 days (e.g., for about 3 days to about 50 days, for about 3 days to about 45 days, for about 3 days to about 40 days, for about 3 days to about 35 days, for about 3 days to about 30 days, for about 3 days to about 25 days, for about 3 days to about 20 days, for about 3 days to about 15 days, for about 3 days to about 14 days, for about 3 days to about 10 days, for about 3 days to about 5 days, for about 5 days to about 60 days, for about 10 days to about 60 days, for about 15 days to about 60 days, for about 20 days to about 60 days, for about 25 days to about 60 days, for about 30 days to about 60 days, for about 35 days to about 60 days, for about 40 days to about 60 days, for about 45 days to about 60 days, or for about 50 days to about 60 days). For example, an organ model can be perfused to establish neovascularization. A pancreas model can be perfused with any appropriate rate and/or pressure. For example, an organ model can be perfused at a rate of from about 0.1 dyne/cm$^2$ to about 10 dyne/cm$^2$ (e.g., about 1 dyne/cm$^2$). In some cases, an organ model can be perfused at a steady rate. In some cases, an organ model can be perfused at a rate (e.g., a shear rate) that changes (e.g., increases, decreases, or oscillates) during a period of perfusion. For example, a pancreas organ model can be perfused with increasing shear rates during day 1 (e.g., from 0 hours to about 24 hours) and at a steady shear rate from days 2-14.

Biomaterials (e.g., pancreatic biomaterials), arrays of organoids (e.g., pancreatic islets), and/or strands of temporary support material can be disposed (e.g., on a model platform) using any appropriate technique. Examples of techniques that can be used to dispose pancreatic biomaterials, arrays of pancreatic islets, and/or strands of temporary support material on a model platform include, without limitation, hanging drop, microwell, micropatterned matrix, microfluidic, acoustic force, and magnetic force based techniques. Methods of fabricating a 3D organ model can be manual, automated, or a combination thereof. In some cases, automated fabrication of a 3D organ model can include bioprinting (e.g., 3D bioprinting). Bioprinting can be done using any appropriate bioprinter (e.g., an inkjet bioprinter). Bioprinting can include droplet-, extrusion-, and/or laser-based bioprinting. In some cases, methods of fabricating organ models can be as described elsewhere (see, e.g., Peng et al., *Trends Biotechnol.* 34:722-32 (2016); and Yu et al., *Scientific Reports,* 6:28714 (2016)).

Figure 8:
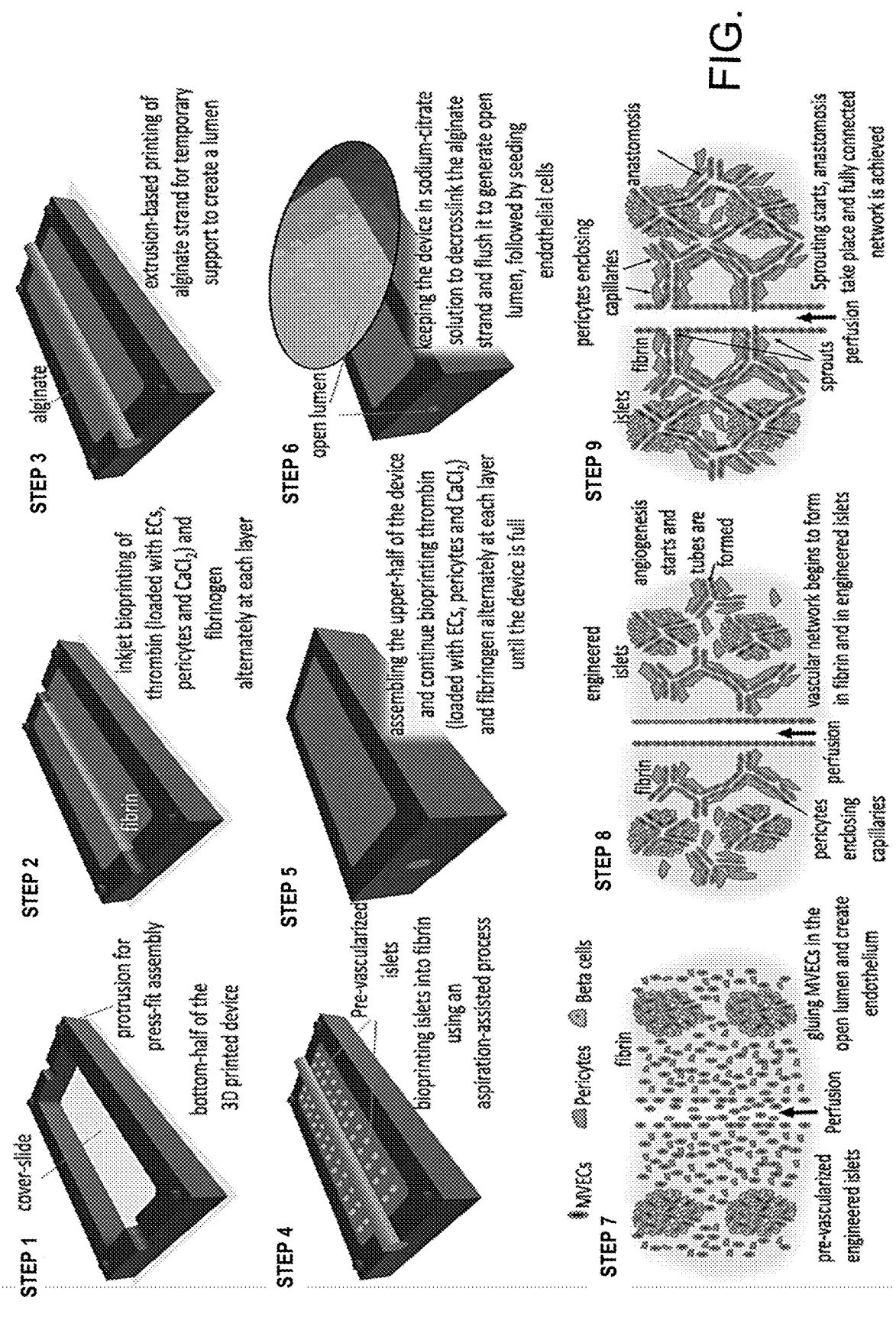
FIG. 8 contains a schematic showing a step-by-step fabrication of an exemplary pancreas-on-a-chip model.

In some cases, a pancreas-on-a-chip model can be made by depositing layers of pancreatic biomaterials (e.g., thrombin, MVECs, pericytes, CaCl$_2$), fibrinogen, alginate strands, fibrin hydrogel, and pre-vascularized islets) on a model platform having a bottom portion and an upper portion. In some cases, a temporary support material can be deposited using extrusion-based bioprinting. For example, a first layer of thrombin, ECs, pericytes, CaCl₂) can be bioprinted in the bottom portion of the model platform, followed by a second layer of fibrinogen bioprinted on the first layer. The first and second layers can be alternated any appropriate number of times (e.g., up to about 14 layers) to fill the bottom portion of the model platform. Alginate strands can be extrusion-printed on the alternating first and second layers (e.g., on the filled bottom portion of a model platform). Pre-vascularized islets (e.g., EPSs) can be bioprinted into a fibrin layer using an aspiration-assisted process. The upper portion of the model platform can be assembled onto the bottom portion, and the first and second layers can be alternately bioprinted until the model platform is full. The model platform can be maintained in a sodium citrate solution to decrosslink the alginate strand and flushed to generate open lumen, followed by seeding MVECs in the open lumen. The model platform can be perfused for about 14 days at a rate of 0.1 dyne/cm² during the first 6 hours, a rate of 1 dyne/cm² thereafter during the first day, followed by a rate of 10 dyne/cm² after the first day to establish a vascular network. An exemplary method of making a functional, 3D, human pancreas model is shown in FIG. 8 and is described in Example 3.

Methods of Using Organ Models

This document provides methods for using functional organ models (e.g., human pancreas models) described herein. In some cases, organ models provided herein can be used for screening drugs (e.g., therapeutic agents). For example, organ models provided herein can be used to evaluate pharmacokinetics (e.g., absorption, distribution, metabolism, and clearance) of a drug. For example, organ models provided herein can be used to evaluate pharmaco-dynamics (e.g., mechanism of action, toxicity, and dose-response relationship (such as efficacy and/or potency)) of a drug. For example, organ models provided herein can be used to identify and/or optimize a drug. In some cases, methods of screening drugs can be high-throughput screening methods. In some cases, methods of screening drugs can include real-time observation.

In cases where an organ model is pancreas model, the pancreas model can be used to screen drugs (e.g., candidate drugs) for treating any appropriate pancreatic disease. Examples of pancreatic diseases include, without limitation, diabetes mellitus (e.g., T1D and type 2 diabetes), pancrea-titis, exocrine pancreatic insufficiency, and cystic fibrosis. For example, a functional pancreas model can be used to screen drugs for treating T1D.

In some cases, organ models provided herein can be used for personalized (e.g., patient-specific) drug screening. For example, in cases where a patient has a pancreatic disease (e.g., T1D), a patient-specific pancreas model can be fabri-cated using ADSC-derived β-cells and ECs (e.g., MVECs) obtained from that patient to engineer patient specific EPSs. A patient can be any appropriate mammal (e.g., a human, mouse, rat, dog, and cat). In some cases, a patient can be a human, and a patient-specific pancreas model can be fabri-cated using ADSC-derived β-cells derived from that human's adipose tissue.

The invention will be further described in the following examples, which do not limit the scope of the invention described in the claims.

EXAMPLES

Example 1: Vascularization of Engineered Pancreatic Spheroids

Despite the recent achievements in cell-based therapies for curing type-1 diabetes (T1D), vascularization of beta (β)-cell clusters is still a major roadblock as it is essential for long-term viability and function of β-cells in vivo. In this Example, micro-vascularization within engineered pancre-atic spheroids (EPSs) made of mouse insulinoma β-TC3 cells and rat heart microvascular endothelial cells (RHMVECs) is provided. Upon culturing in three-dimen-sional (3D) hydrogel constructs under angiogenic condi-tions, EPSs sprouted extensive capillaries into the surround-ing matrix. Ultra-morphological analysis through histological sections also revealed duct-like lumens within EPSs showing the presence of neovascularization within spheroids. EPSs cultured in hydrogel constructs maintained their viability and functionality over time, while non-vas-cularized EPSs, without the presence of RHMVECs, could not retain their viability nor functionality. Micro-vascular-ization of engineered islets is demonstrated, where patient-specific stem cell-derived human beta cells can be combined with micro-vascular endothelial cells for an effective treat-ment of T1D.

Materials and Methods

Cell Culture

Mouse insulinoma β TC3 cells (βTC3s) were cultured in Dulbecco's Modified Eagle's Medium (DMEM; Corning Cellgro, Manassas, VA) supplemented with 20% fetal bovine serum (Life Technologies, Grand Island, NY), 1 mM sodium pyruvate (Life Technologies), 2 mM GLUTA-MAX™ (Life Technologies), and 100 U/mL penicillin G, 100 μg/mL streptomycin (Life Technologies). Rat heart microvessel endothelial cells (RHMVEC) (VEC Technolo-gies, Rensselaer, NY) were cultured in MCDB 131 medium (Corning Cellgro) supplemented with 5% fetal bovine serum, 2 mM GLUTAMAX™, 1 g/mL hydrocortisone (Sigma-Aldrich, St. Louis, MO), 1 μg/mL human epidermal growth factor (Sigma-Aldrich), 12 μg/mL bovine brain extract (Lonza, Walkersville, MD), and 100 U/mL penicillin G, 100 μg/mL streptomycin. Cells were maintained at 37° C. in a 5% CO₂ humidified atmosphere. Cell culture medium was changed every 2-3 days. Subconfluent cultures were detached from the flasks using a 0.25% trypsin-0.1% EDTA solution (Life Technologies) and split to maintain cell growth. Passages 9 through 15 and 10 through 22 were used for βTC3 and RHMVEC, respectively.

Mold Fabrication for 3D Culture

Negative patterns were designed with cylindrical micro-pillars of different diameters on top of the mold surface. PTC Creo software (Parametric Technology Corporation, Exton, PA) was used to create a 3D computer aided design (CAD) model. The CAD model was then converted to a stereo-lithography (STL) file to fabricate the mold using a Perfac-tory® Micro Hi-Res 3D printer (EnvisionTec, Detroit, MI). A high-resolution material, HTM140M, (EnvisionTec) was used to manufacture the mold. The cylindrical micro-pillars were 300 μm in diameter with a total number of 124 wells. After 3D printing the HTM140M negative mold, it was detached from the base, washed with detergent, then with 70% ethanol, and sterilized under UV light for 15 minutes. To cast the mold, 1.5% (w/v) agarose (RPI Corp., Mt. Prospect, IL) was dissolved in MILLI-Q® water, then autoclaved. Liquefied agarose was poured carefully into the negative mold and left to solidify for 1 hour at room temperature; agarose molds were then detached from the wall of 3D printed form with needle, and removed by strong concussion into 100 mm Petri dishes. Prepared agarose molds were incubated for 10 minutes in two changes of appropriate culture medium then stored under sterile conditions at 4° C.

Fabrication of Engineered Pancreatic Spheroids (EPSs)

On reaching 70% confluence, βTC3 and RHMVEC were detached from cell culture flasks using trypsin; cell media was added to deactivate trypsin, and suspension was centrifuged for 5 minutes at 1,600 rpm. Cells were counted using a hemocytometer. βTC3 and RHMVEC, respectively, were combined in ratios of 1:1 or 2:1. Also a third ratio was created by βTC3-only cells. A total of 2 million cells were suspended in 100 µL of medium and carefully pipetted on the top chamber of the agarose mold. Gravity acts to pull cells down into the agarose wells where cells aggregate as described elsewhere (see, e.g., Napolitano et al., *Biotechniques*, 43:494-500 (2007)). Over the next 9 hours, at 3 hour intervals, a small amount (~150 µL) of fresh medium was gently added to the top of the mold to provide nutrition for the developing EPSs. The petri dish containing the molds was also filled with cell culture media to ensure proper hydration of agarose molds. After 12 hours, EPSs compacted and media was changed every 24 hours.

Morphological Analysis

EPSs formed using βTC3-only, a 1:1 ratio of βTC3 cells to RHMVEC cells, or a 2:1 ratio of βTC3 cells to RHMVEC cells were assayed for size and proliferation at three time points: 1, 5, and 10 days. At each time point, the size of 15 random EPSs for three cell ratios in concentrations of 1, 2, and $3 \times 10^6$ cells/mold was measured using an EVOS® FL Auto inverted microscope (ThermoFisher, Pittsburgh, PA) and software in bright field mode. The relative difference in average diameter between $1^{st}$ and $10^{th}$ day was determined by the equation:

$$\frac{(v_2 - v_1)}{|v_1|} \times 100.$$

The morphology of EPSs was determined by razor cutting of the agarose mold containing EPSs. EPSs were observed and imaged on the EVOS® FL Auto (Thermofisher) inverted light microscope to visualize mold characteristics and EPS morphology vertically dimension.

Scanning Electron Microscopy (SEM) Imaging

Field emission scanning electron microscopy (SEM) (Zeiss SIGMA VP-FESEM) was used to investigate the surface topography of EPSs. EPSs were harvested after three days of culture in the agarose mold and fixed in 4% paraformaldehyde (Sigma Aldrich) overnight. EPSs were then carefully washed in PBS and dehydrated using graded ethanol solutions (25% to 100%). To ensure complete removal of water, EPSs were then further dried in a critical point dryer (CPD300, LEICA® EM). On complete dehydration, EPSs were sputter coated with gold using the Bal-tec SCD-050 Sputter Coater (LEICA®, Wetzlar, Germany) and observed at an accelerating voltage of 3 kV.

Transmission Electron Microscopy (TEM) Imaging

Transmission electron microscopy (TEM) was performed using the Tecnai $G^2$ 20 equipment (FEI Company, Hillsboro, OR). EPSs were fixed in 4% paraformaldehyde (Sigma Aldrich, USA) for 30 minutes and then centrifuged shortly to form a pellet and quickly washed in 0.1 M cacodylate buffer. The pellet was then subjected to 1% $OsO_4$ treatment for 60 minutes. After the $OsO_4$ treatment, the pellet was carefully washed in the cacodylate buffer again for 10 minutes. Following this, En Bloc staining was carried out using 2% uranyl acetate diluted in 50% ethanol for 30 minutes. Samples were then dehydrated using graded ethanol solutions (50%-95%) on ice and in propylene oxide before finally embedding them in epoxy resin. Following the epoxy embedding, 70 nm sections of the specimen was obtained by ultramicrotomy (UC6, LEICA® EM) followed by mounting on TEM grids. The grids were stained post-sectioning with uranyl acetate and lead citrate to increase the contrast and observe cellular level details.

Culturing EPSs in Fibrin Constructs

Fibrin hydrogel was prepared by blending fibrinogen protein isolated from bovine plasma (Sigma-Aldrich) and bovine thrombin from plasma (Sigma-Aldrich). Both solutions were dissolved separately in DPBS in the following concentration: 10 mg/mL fibrinogen and 3 U/mL thrombin at the 37° C. Both components were combined in equal amounts yielding a final concentration of 5 mg/mL fibrinogen and 1.5 U/mL thrombin. EPSs were gently suspended in thrombin, which is blended with fibrinogen. After gentle, thorough pipetting, the pre-crosslinked suspension was deposited on 12 mm round cover slips placed in a 24-well plate. After 15 minutes of crosslinking in the incubator, cell media was deposited on top of fibrin. The constructs culture medium was formulated in 1:1 ratio of βTC3 media and EGM-2V media (Lonza). Fabricated fibrin constructs were installed into a live cell imaging chamber and observed using a Keyence BZ-9000E microscope (Keyence Corp, Boston, MA). Images were captured every hour for a 65-hour period.

Cell Viability and Proliferation

Three ratios of EPSs (EPSs formed using βTC3-only, a 1:1 ratio of βTC3 cells to RHMVEC cells, or a 2:1 ratio of βTC3 cells to RHMVEC cells), alone and embedded in fibrin, were stained to determine the viability at three time points, 1, 5, and 10 days. EPSs were removed from the agarose well and rinsed three times with DPBS (Life Technologies). A 300 µL of DPBS containing 2 µM calcein-AM (Invitrogen, Carlsbad, CA) and 4 µM ethidium homodimer (Life Technologies) was added to the EPSs or fibrin constructs. Plates were protected from light and incubated at 37° C. in 5% $CO_2$ for up to 3 hours followed by rinsing with DBPS three times. Free-standing EPSs and those embedded in fibrin were transferred to the glass-bottom dishes for imaging on confocal laser scanning microscopy (Olympus FV10i, Olympus, America Inc., Center Valley, PA) to detect calcein (excitation 499, emission 520) and ethidium homodimer (excitation 577, emission 603). Ten representative areas of each sample type, ratio, and time point were randomly selected for imaging. Viability was quantified using ImageJ (National Institutes of Health). A minimum of 180 EPSs from three separate runs were quantified.

Proliferation of cells was determined by a 3-(4,5-Dimethylthiazol-2-yl)-2,5-Diphenyltetrazolium Bromide (MTT) assay (Life Technologies). EPSs from one, full mold were used per each time point for each cell ratio. The same amount of cells served for the proliferation measurement, since cells were seeded in each mold in equal quantity. EPSs were flushed from agarose wells, washed twice with Dulbecco's phosphate buffered saline (DPBS; Life Technologies), and suspended in 100 µL of the media without phenol red. To each sample, 10 µL of 12 mM MTT solution was added; a negative control consisted of cell medium without cells. All samples and control were incubated at 37° C. for 4 hours. All but 50 µL of the reaction solution was removed and 100 µL of DMSO (Sigma-Aldrich) was added, thoroughly mixed with and incubated at 37° C. for 10 minutes. Samples were mixed again and the absorbance was read immediately at 540 nm on a Powerwave X-340 spectrophotometer (BioTek, Winooski, VT) and the data was generated by KCjunior software (Biotek).

Immunostaining Imaging

To determine the cell distribution within sprouting EPSs, immunostaining was performed using a rabbit anti-platelet endothelial cell adhesion molecule (PECAM-1) antibody (Ab28364, Abcam, Cambridge, MA) to label the RHMVEC and guinea pig anti-insulin antibody (Ab7842, Abcam) for βTC3. Nuclei were stained with Hoechst 33258 (ThermoFisher).

The EPSs embedded within the fibrin were cultured in a 24-well plate for 3 days and then fixed overnight with 4% paraformaldehyde (Sigma-Aldrich) at 4° C. Constructs were then washed 3 times (10 minutes each in DPBS) at room temperature. Permeabilization was performed with 0.25% TRITON™ X-100 (Sigma-Aldrich) and 5% normal goat serum (Abcam) diluted in DPBS and incubated for 1 hour. Primary antibodies were diluted in blocking solution (1:50 for PECAM-1 and 1:200 for insulin) applied to constructs. After overnight incubation at 4° C., samples were washed 3 times (10 minutes each in DPBS). PECAM secondary goat anti-rabbit antibody (ALEXA FLUOR™ 647, Life Technologies) diluted 1:500, was incubated within the constructs for 1 hour at room temperature in dark and then washed for 10 minutes in DPBS. Then, insulin goat anti-guinea pig secondary antibody (ALEXA FLUOR™ 568, Life Technologies) diluted 1:500, was incubated within the constructs for 1 hour at room temperature in dark. Staining was followed by 10 minutes DPBS wash and incubated for 30 minutes in 5 μg/mL Hoechst. Samples were washed three times per 10 minutes in DPBS, followed by quick rinse in distilled water and then placed on a droplet of VECTASHIELD® (Vector Laboratories) on glass-bottom dishes for imaging on a confocal laser scanning microscope (Olympus FV10i) by lasers ALEXA FLUOR™ 568 (excitation 577, emission 603) and ALEXA FLUOR™ 647 (excitation 653, emission 668). Images were pseudo-colored, green for PECAM and red for insulin.

Insulin Secretion Analysis

EPSs formed from the three cell mixing ratios were grown for 72 hours prior to the insulin secretion analysis. The two-dimensional (2D) culture was performed as a comparison control to EPSs. Two million cells for each control were seeded per tissue culture dish, which is as an equivalent of the cell amount in a single mold of EPSs. The insulin secretion analysis was conducted at 3 time points (1, 5, and 10 days) of βTC3-only, 1:1 ratio of βTC3 to RHMVEC, and 2:1 ratio of βTC3 to RHMVEC, and one-day, 2D culture of βTC3-only, 1:1 ratio of βTC3 to RHMVEC, and 2:1 ratio of βTC3 and RHMVEC, respectively. Following this, 1× Krebs buffer was freshly prepared (25 mM HEPES, 115 mM NaCl, 24 mM $NaHCO_3$, 5 mM KCl, 1 mM $MgCl_2$, 0.2 g 0.1% BSA dissolved MQ $H_2O$). To the final solution was added 2.5 mM $CaCl_2$) and the pH was adjusted to 7.4 with 1 M NaOH. This solution was filtered through 0.22 μm filter and stored at 4° C.

Only a single glucose stimulation was performed due to unresponsive character of βTC3 cells on elevated glucose level. Therefore, 2.8 mM glucose solution was prepared in the 1× Krebs buffer. All of the EPSs (e.g., EPSs formed using βTC3-only, 1:1, and 2:1 ratio of βTC3 and RHMVEC, respectively), as well as 2D cultures of the same cell ratios, were shortly rinsed in a glucose solution and then incubated in a fresh solution for 1 hour in 37° C. and 5% $CO_2$. After incubation, 100 μL of solution of the supernatant was kept in −20° C. for the insulin enzyme-linked immunosorbent assay (ELISA) analysis. Mouse ultrasensitive insulin ELISA kit (Alpco, Salem, NH) was used to detect insulin secretion of EPSs and 2D cultures after glucose simulation test at $1^{st}$, $5^{th}$, and $10^{th}$ day of experiments. Samples were gently mixed, and centrifuged at 2,000 rpm for 5 minutes to remove cell debris. ELISA protocol was performed according to manufacturer's instruction. Briefly, 5 μL of standard solution or sample was applied in duplicate wells of the pre-coated ELISA microplate and then, 75 μL of HRP conjugate was added. Plate was incubated for 2 hours on a shaker (300 rpm) and then rinsed thoroughly 6 times with wash buffer. After careful removal of the final wash, 100 μL of TMB substrate was pipetted into each well; plate was incubated for 30 minutes on a platform shaker protected from light. Afterward, 100 μL of stop solution was added into each well. Absorbance readings were performed at 450 nm on a Powerwave X-340 spectrophotometer (BioTek) and insulin concentrations were calculated by KCjunior software.

Quantification of Endothelial Sprouting

Images of EPSs encapsulated in fibrin were taken at each at day 1, 3 and 5 on the EVOS® FL Auto (Thermofisher). These images were then processed on ImageJ software (NIH) using the Angiogenesis Analyzer plugin to generate a skeleton of the sprouts. The generated skeleton was further analyzed using the Analyze Skeleton plugin to quantify the sprout length and number. The average sprouting length and the average sprout number was calculated for a set of 10 spheroids for each ratio (e.g., EPSs formed using a 1:1 ratio of βTC3 to RHMVEC, and a 2:1 ratio of βTC3 to RHMVEC) at each time point (day 1, 3, and 5).

Histology Study

EPSs in three ratios (e.g., EPSs formed using βTC3-only, a 1:1 ratio of βTC3 to RHMVEC, and a 2:1 of βTC3 to RHMVEC) embedded in fibrin on the 12 mm round cover slips were cultured for 5 days in 24-well plate. The EPSs-laden fibrin was stabilized by adding 300 μL of 1.5% agarose (RPI Corp.) on the top, prior fixation in 4% (v/v) paraformaldehyde overnight. The constructs were gradually dehydrated in alcohol and sectioned at 8 μm. Sections were then stained by LEICA® Autostainer XL (LEICA®). Briefly, sections underwent deparaffinization in xylene substitute followed by rehydration with two decreasing ethanol concentrations (100 and 95%). The sections were then washed with deionized water and stained with hematoxylin 560 (LEICA®) for 4.5 minutes. Next, the stained sections were washed with water and decolorized with acid alcohol. Then, slides were treated with a bluing buffer 8 (LEICA®) and immediately washed with water. It was followed by ethanol for 1 minute, eosin Y (LEICA®) staining for 20 seconds, dehydration with 3 increasing concentrations of ethanol (80, 90, and 100%), and xylene substitute. Sections were mounted by Xylene Substitute Mountant (Thermofisher) and dried overnight. The slides were viewed under the Olympus BX51 (Olympus), and images were taken with the manufacturer's software.

Statistical Analysis

Due to the large number of data points analyzed, average EPS diameters are shown as the mean, and the error bars represent the standard deviation from the mean. All other data are reported as the mean with error bars indicating the standard error of the mean. Statistical significance was determined using a one-tailed Student's t-test using (MINITAB, State College, PA). Results were considered significant with a confidence level of 95%, where $p < 0.05$ (*), $p < 0.01$ (), and $p < 0.001$ (*).

Results

EPS Fabrication and Characterization

Figures 2A, 2B:
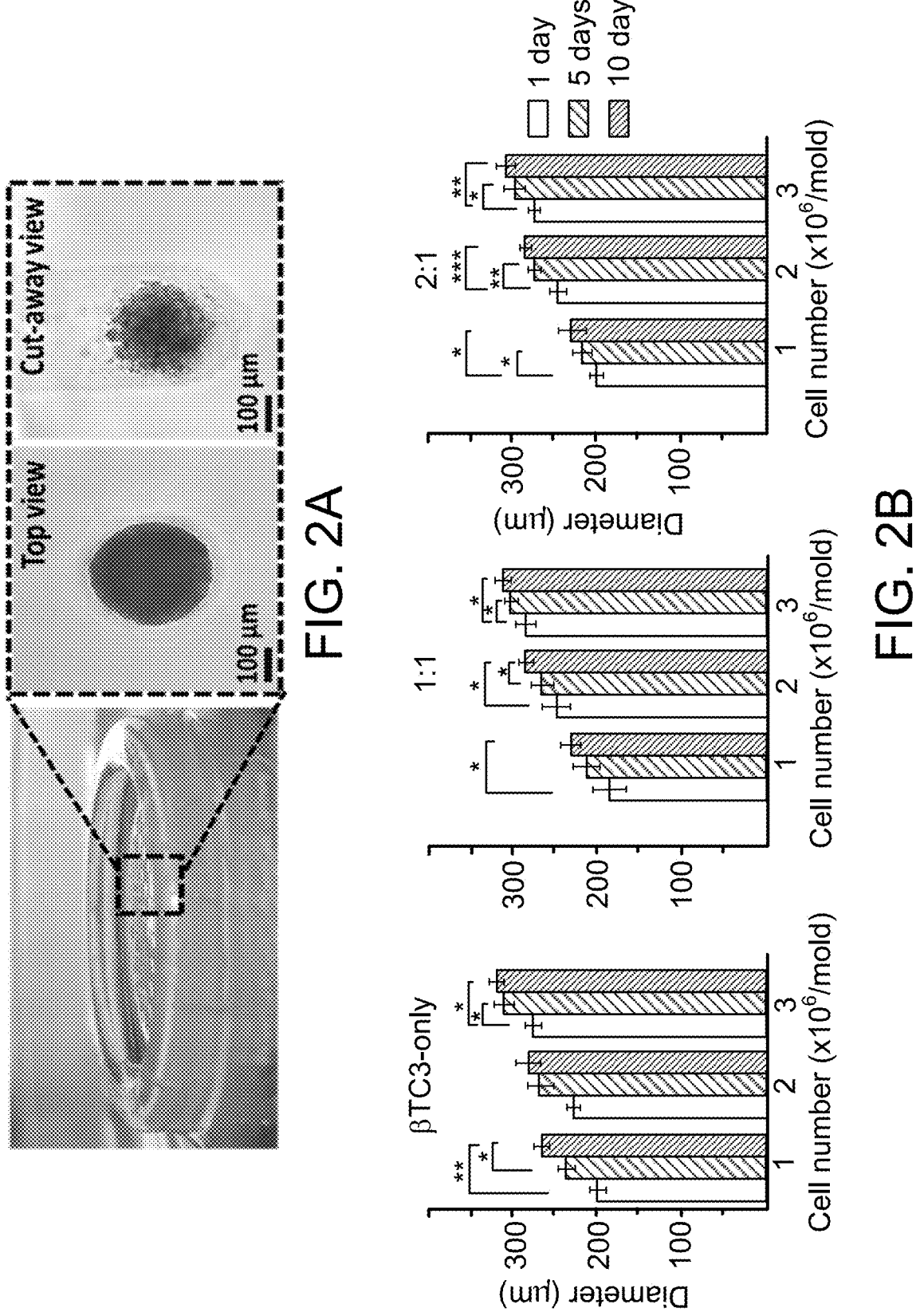
FIG. 2 shows EPS fabrication and morphology. (A) FIG. 2A contains photographs of an agarose mold in a Petri dish surrounded by cell culture media (left), an EPS on the top view (middle), and the cut-away view of an agarose mold showing EPS at the bottom of a microwell on day 3 (right). (B) FIG. 2B contains bar graphs showing that EPS diameter changed over time (1, 5, and 10 days) for three different cell seeding ratios: βTC3-only (left), a 1:1 ratio of βTC3 cells to RHMVEC cells (middle), and a 2:1 ratio of βTC3 cells to RHMVEC cells (right). (C) FIG. 2C contains SEM images of three-day cultured EPSs shown with a magnification of the surface (morphology) for βTC3-only (left), a 1:1 ratio of βTC3 cells to RHMVEC cells (middle), and a 2:1 ratio of βTC3 cells to RHMVEC cells (right).

Agarose has been extensively used for molds that facilitate cell fusion. In order to create a multi-well agarose mold, negative molds were designed in the PTC Creo software, shown in FIG. 1A. The printed plastic mold (FIG. 1B) was characterized by high resolution of fine details and a superior surface finish. When filled with liquefied agarose, the mold formed a reproducible uniform hydrogel having 124 microwells and a 300 μm diameter, as shown in FIG. 2A (left). After 24 hours of incubation in the agarose mold, EPSs exhibited a compact and rigid morphology (see FIG. 2A, right) that capable of being flushed out of the mold with a gentle pipetting.

In this investigation, βTC3 and RHMVEC were co-cultured for EPSs formation in three ratios, βTC3-only, a 1:1 ration of βTC3 to RHMVEC, and a 2:1 ratio of βTC3 to RHMVEC. In EPSs, βTC3s provided the insulin-secreting component, and RHMVEC served to strengthen EPS formation and generate internal and external neovascularization. Cells seeded in biocompatible, non-toxic, mechanically stable, and non-adhesive agarose molds aggregated successfully (see FIG. 2A), and cell distribution was uniform throughout the microwell.

EPS diameters were measured at 1, 5, and 10 days (FIG. 2B). The average diameter of βTC3-only spheroids seeded at $1\times10^6$ cells/mold measured 202.2±8.88 μm on day 1, 238.8±8.93 m on day 5, and 269.3±8.45 μm on day 10. The average size increase was over 33% over a ten-day period. A similar trend was observed when βTC3 were seeded at $2\times10^6$ cells/mold; average EPS diameter ranged from 228.9±6.77 μm on day 1, 269.8±15.2 μm on day 5, and 285.8±11.4 μm on day 10, increasing over 24%. βTC3-only group seeded at $3\times10^6$ cells/mold, average EPS diameter measured 278.4±5.98 μm on the $1^{st}$ day, 314.2±10 μm on the $5^{th}$ day, and 321.95±7.32 μm on the $10^{th}$ day. The average size increase was only 15.6% over a ten-day period suggesting that the microwell size limits the maximum diameter of the EPS. Similar results were seen in EPSs formed from 1:1 and 2:1 ratios of βTC3 to RHMVEC. When $1\times10^6$ cells/mold were seeded in 1:1 ratio EPS diameters were 186.7±20.5 μm (day 1), 215.8±15.88 μm (day 5) and 233.5±10 μm (day 10) while the diameter for 2:1 ratio was measured 201.3±6.89 μm (day 1), 218.9±10.7 μm (day 5) and 231.2±14.6 μm (day 10). Average diameter increase was 25.1% and 14.8% for 1:1 and 2:1 ratios of βTC3 to RHMVEC, respectively. Using $2\times10^6$ cells/mold, the average EPS diameter was 251.6±17.76 μm (day 1), 267.5±12.6 μm (day 5), and 289.08±9.42 μm (day 10) for 1:1 ratio. For the 2:1 ratio, EPS measured 247.3±8.98 μm (day 1), 276.3±5 μm (day 5) and 285.5±6.87 μm (day 10). The average size increased by 14.9% (1:1) and 15.4% (2:1) over the 10-day period. Finally, cells seeded at 1:1 ratio of βTC3 to RHMVEC using $3\times10^6$ cells/mold measured 288.15±8.61 μm on the $1^{st}$ day, 306.31±6.93 μm on the $5^{th}$ day, and 314±10.93 μm on the $10^{th}$ day. The 2:1 ratio of βTC3 to RHMVEC yielded similar results measuring 275.3±6 μm on the $1^{st}$ day, 301.1±13.22 μm on the $5^{th}$ day, and 308.7±11.25 μm on the $10^{th}$ day. The average size increased by 9% (1:1) and 12.1% (2:1) over the 10-day period. The reduced increase could be explained by the limited microwell diameter and the lack of nutrient penetration to the EPS core. Also, the strong adhesion exhibited by RHMVECs and the ECM components produced by RHMVECs could contribute to the limited expansion of the EPS. EPSs exhibited expansion in their diameter under all seeding conditions, suggesting cell proliferation, proper growth conditions and a synergistic relationship between the pancreatic and vascular cell lines. Based on growth rate and the necessity to maintain an average diameter below 300 μm, $2\times10^6$ cells/mold was used for the rest of the study.

Figure 2C:
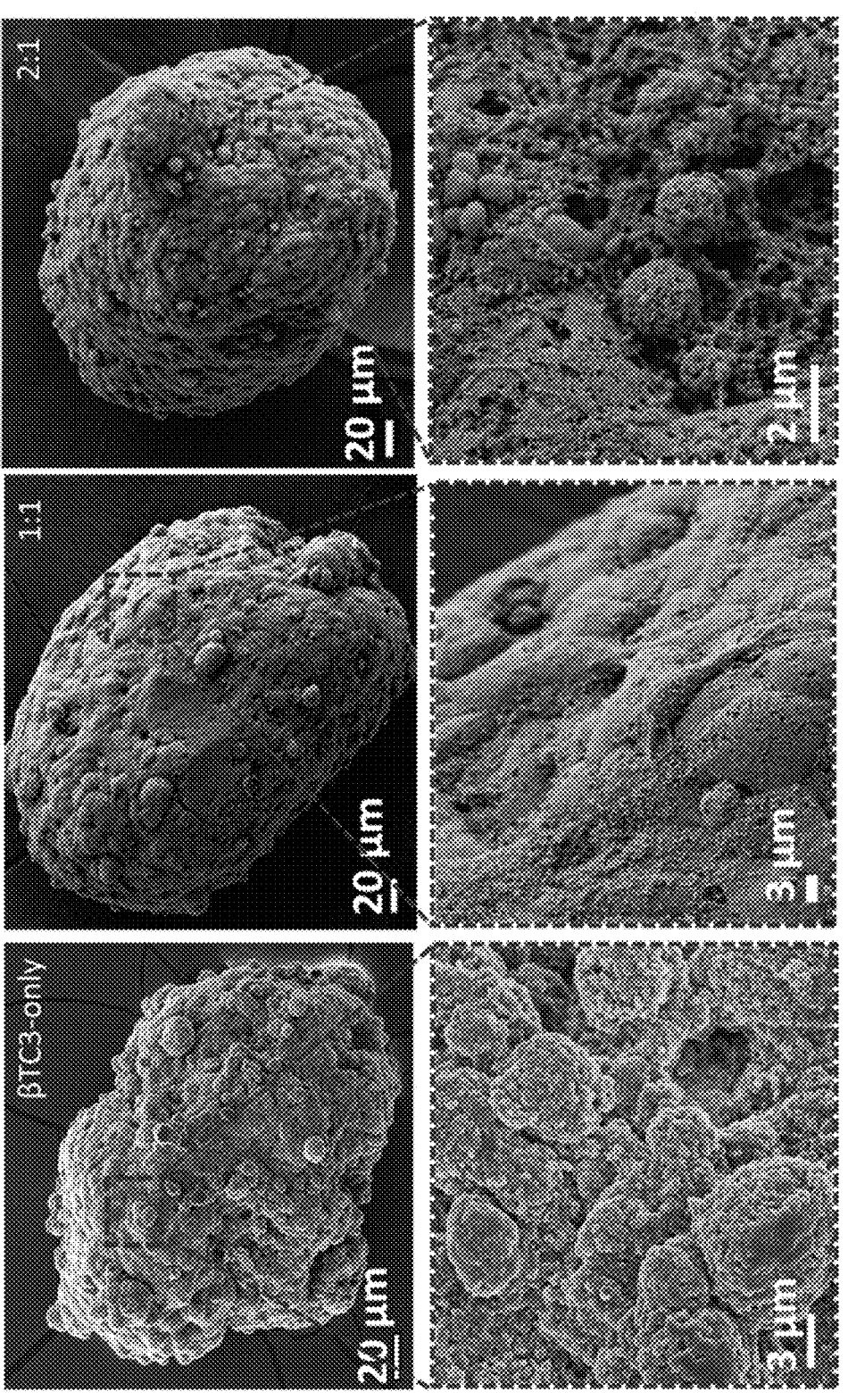

The SEM images on three days-old EPSs demonstrated solid, compact and spherical-shaped structure (FIG. 2C). The ECM was deposited by cells and is presented as slightly irregular crown on the surface, which was magnified in the bottom row of FIG. 2C. Endothelial cells contribute directly to synthesizing the ECM, which includes collagen type IV and laminin and serves as physical barrier for immune system cells. Therefore, in EPSs formed from a 1:1 ration of βTC3 to RHMVEC and EPSs formed from a 2:1 ratio of βTC3 to RHMVEC the higher amount of ECM is deposited and EPS in this ratios are characterized by smoother surface topology.

Cell Viability and Proliferation

Figure 3:
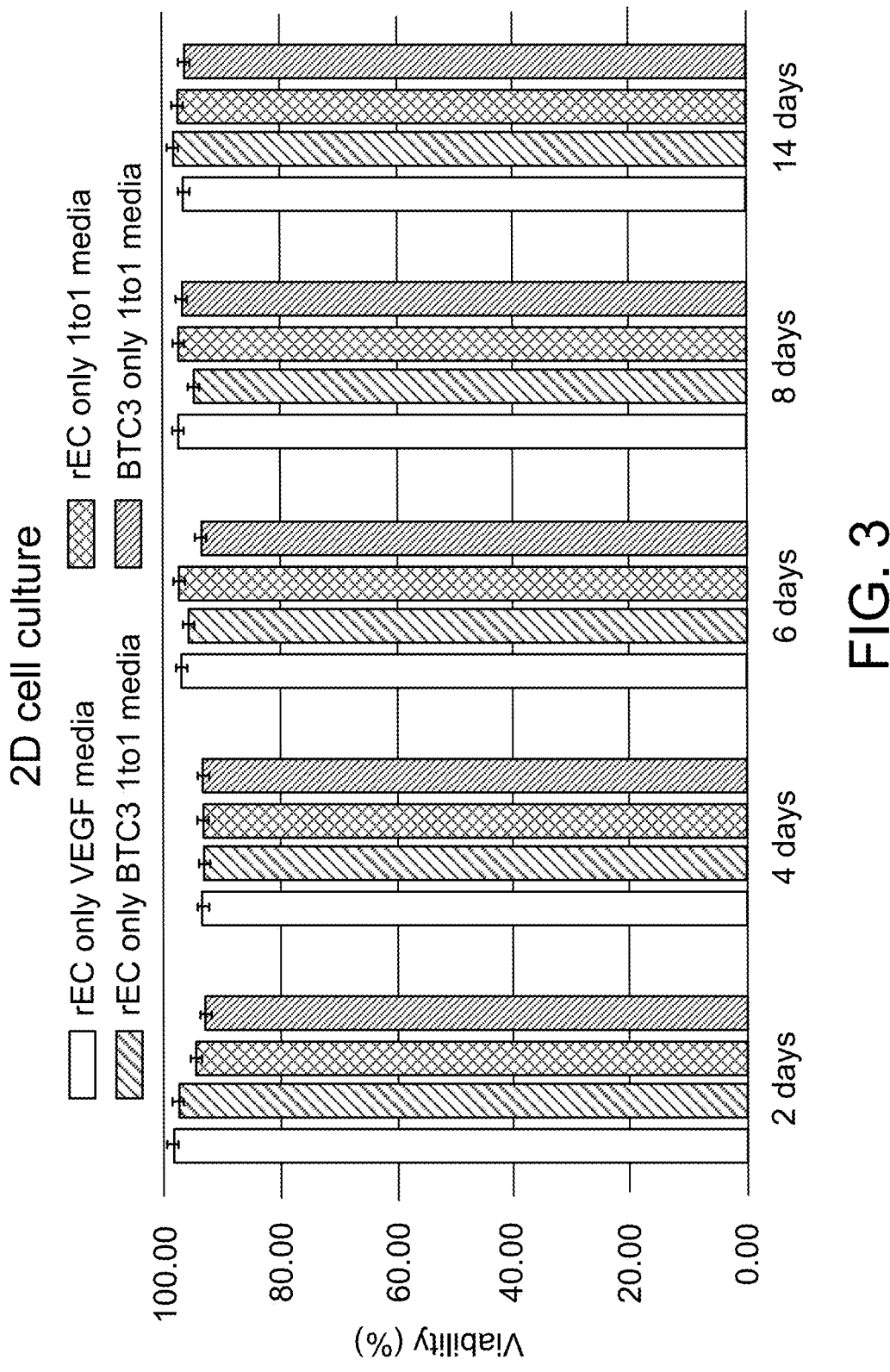
FIG. 3 contains bar graphs showing cell viability of two dimensional (2D) co-cultures.

Cell viability in 2D cell culture was detected over a 14-day culture, for RHMVECs only cultured in VEGF media, RHMVECs only cultured in 1:1 media, βTC3 cells only cultured in 1:1 media, and RHMVECs and βTC3 cells co-cultured in 1:1 media (FIG. 3). The viability did not change significantly over the 14-day culture.

Figure 4A:
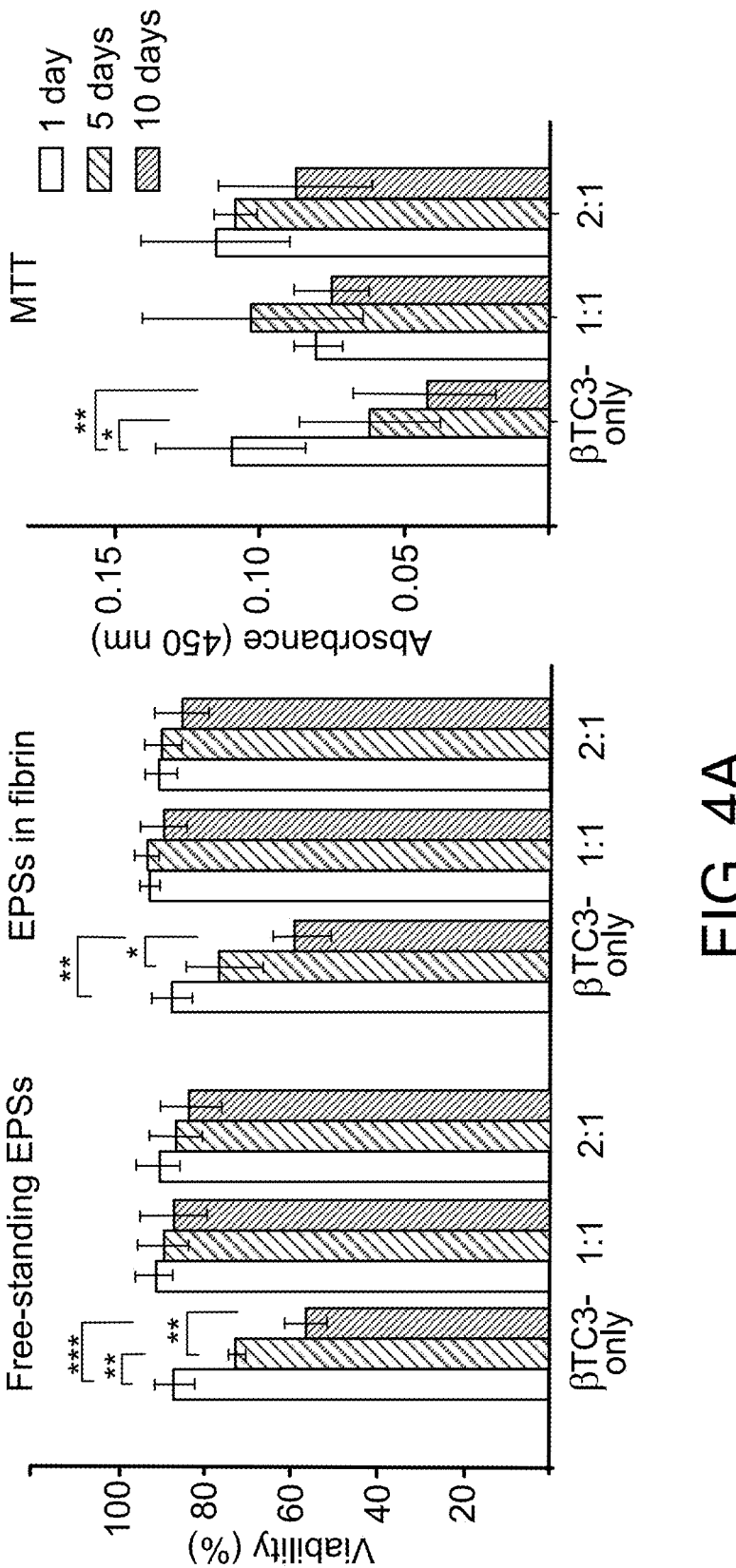
FIG. 4 shows EPS cell viability. (A) FIG. 4A contains bar graphs showing a quantification of cell viability on free-standing EPSs (left) and EPSs embedded in fibrin (middle) over 1, 5, and 10 days. The right panel depicts the proliferation rate conducted on MTT assay over the same time points. (B) FIG. 4B contains representative pictures of live/dead staining at 1 (top row), 5 (middle row), and 10 (bottom row) days of free-standing EPSs (left panel) and EPSs embedded in fibrin (right panel). EPSs were cultures using βTC3-only (left), a 1:1 ratio of βTC3 cells to RHMVEC cells (middle), or a 2:1 ratio of βTC3 cells to RHMVEC cells (right).

Cell viability in EPSs was detected over a 10-day culture, for both free-standing EPSs and EPSs embedded in fibrin (FIG. 4A).

The average viability of free-standing βTC3-only EPSs was 87.41±4.24% on day 1, 73.25±1.02% on day 5, and 56.44±5.09% on day 10. The average viability decreases significantly (by over 35%) over the 10-day period. This trend was not observed for EPSs formed from a 1:1 ratio of βTC3 to RHMVEC, where the average viability was 91.62±4.3% on day 1, 89.59±5.78% on day 5, and 87.51±7.4% on day 10. In EPSs formed from a 2:1 ratio of βTC3 to RHMVEC, the cell viability was 90.82±4.54% on the 1st day, 86.82±5.75% on the $5^{th}$ day, to 83.15±7.1% on the $10^{th}$ day. The viability did not change significantly neither for 1:1 nor 2:1 over the 10-day culture. Strongly decreasing tendency in viability in βTC3-only EPSs suggest that presence of RHMVECs increased the viability of EPSs.

The other investigation was performed over the same period of time for EPSs embedded in fibrin (FIG. 4A middle), where similar tendencies were noted. The average viability of βTC3-only group was 86.09±4.38% on day 1, 75.58±7.14% on day 5, and 58.19±4.81% on day 10. The average all viability decreased by 32.41% over the 10-day period. Such trend was not observed in 1:1 group, where the average viability was 90.91±1.96% on day 1, 91.59±2.29% on day 5, and 87.75±5.11% on day 10. In EPSs formed from a 2:1 ratio of βTC3 to RHMVEC, cell viability was 88.56±3.43% on the $1^{st}$ day, 88.21±3.94% on the $5^{th}$ day, and 83.7±5.97% on the $10^{th}$ day.

The MTT results (FIG. 4A, right) revealed that proliferation of βTC3-only significantly decreased over time, by 61.12% between 1 and 10 days. The 1:1 and 2:1 ratio EPS exhibited a stable proliferation rate, which did not differ significantly over time. It indicated that 3D co-culture of βTC3 and RMHVEC supports the proliferation rate and confirmed the live/dead staining results.

Free-standing βTC3-only group were very fragile after couple days in culture. Spheroids disaggregated easily, also during the extraction out of the mold. However, during culture, EPSs were surrounded with fresh media within immediate contact among 10 days. The situation looked differently with βTC3-only group embedded in fibrin, where the media was added onto of the fibrin construct and, therefore, βTC3-only group had limited exposure to media. Decrease in the viability after 10 days was similar for free-standing and embedded in fibrin βTC3-only.

Figure 4B:
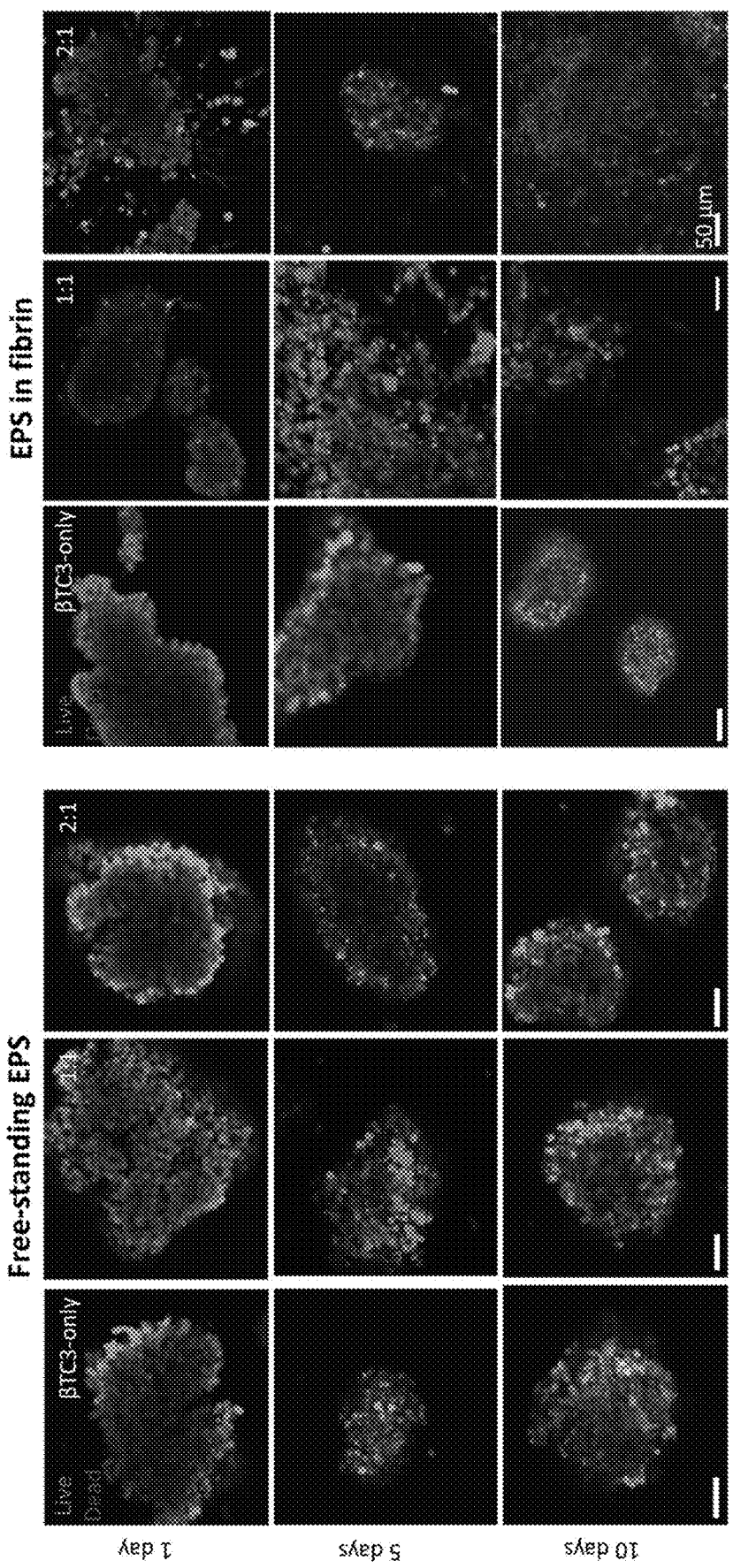

Both EPSs formed from a 1:1 ratio of βTC3 to RHMVEC and EPSs formed from a 2:1 ratio of βTC3 to RHMVEC, maintained their viability in a high level. The representative pictures from live/dead staining were presented in the FIG. 4B, for both free-standing (left panel) and embedded in fibrin EPS (right panel) for each time point and cell ratio. Viability in fibrin could be maintain in a high level due to expansive character of RMHVEC.

Functional Analysis of EPSs

Figure 5A:
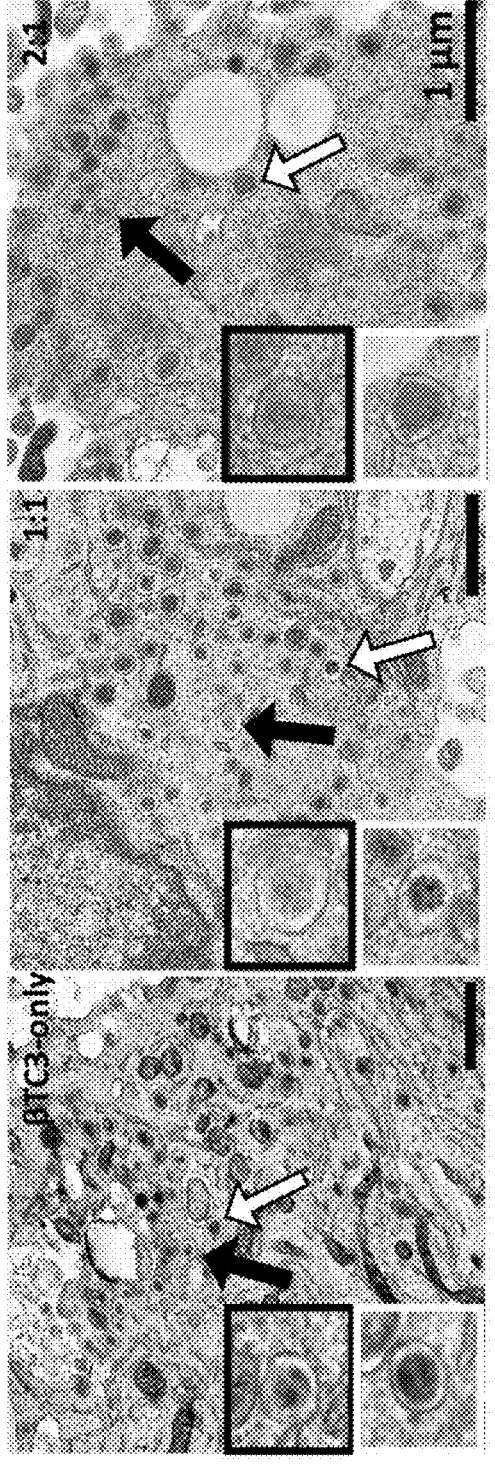
FIG. 5 shows EPS functionality. (A) FIG. 5A contains microscope images of ultra-morphology of aggregates showing the vesicles containing insulin granules in each ratio: βTC3-only (left), a 1:1 ratio of TC3 cells to RHMVEC cells (middle), and a 2:1 ratio of βTC3 cells to RHMVEC cells (right). The arrows demonstrate immature (black) and mature (grey) insulin granules. (B) FIG. 5B contains microscope images of immunocytochemistry of EPSs with RHMVECs stained for PECAM, βTC3 insulin, and nuclei.

In the TEM study, the insulin granules were visible in 70 μm thick sections of EPSs. These unique granules for beta-cells, were visible in different stages of maturation and were surrounded by characteristic halo and membrane (as described elsewhere; see, e.g., Fava et al., *Diabetologia*, 55:1013-1023 (2012)). The granules were present in EPSs formed from a 1:1 ratio of βTC3 to RHMVEC and in EPSs formed from a 2:1 ratio of βTC3 to RHMVEC (FIG. 5A) in both immature and mature state. Early insulin granules had larger, sparse granule with faded membrane (FIG. 5A, black arrows); the mature had a dense core and clearly defined membrane (FIG. 5A white arrows). The insulin granules of βTC3 cells, a mouse insulinoma cell line, had a diameter not exceeding 250 nm that corresponds to the size of rat insulin granules (243 nm) as described elsewhere (see, e.g., Fava et al., *Diabetologia*, 55:1013-1023 (2012)).

Figure 5B:
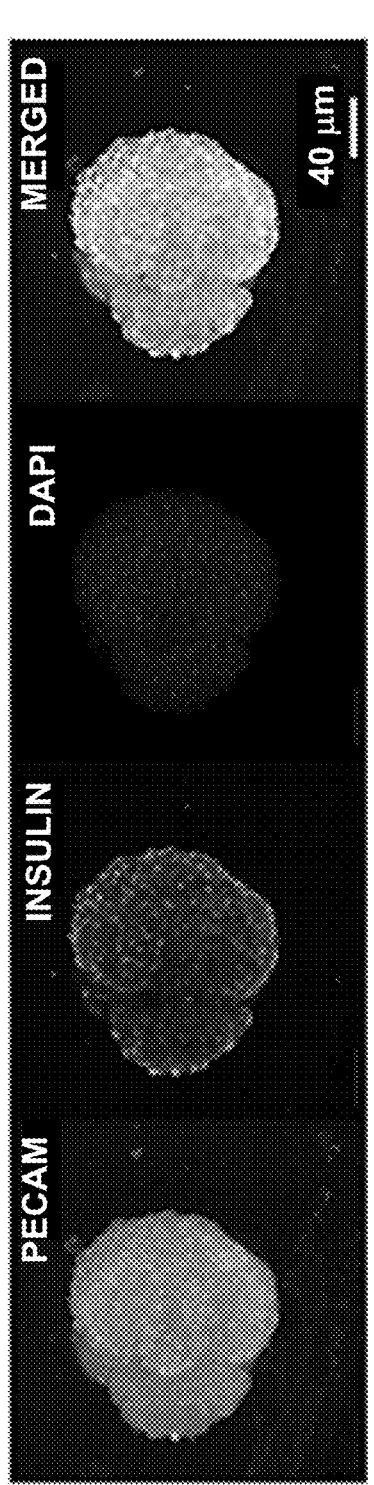

Free-standing EPSs formed from a 1:1 ratio of βTC3 to RHMVEC and EPSs formed from a 2:1 ratio of βTC3 to RHMVEC, were immunostained for insulin to label the βTC3 cells, and PECAM-1 antibody to identify for endothelial cells. Nuclei were stained with DAPI. The confocal images, shown in FIG. 5B, indicated uniform distribution of each cell type among EPSs. Formation of neovascularization was not detected within free-standing EPSs.

Vascularization

EPSs were seeded within fibrin hydrogel to induce vascularization. Over 65 hours of culture, EPSs were observed to form an extensive vascularization (see FIG. 6A). Endothelial sprouts developed approximately 20 hours after seeding and formed a more complex vasculature over time. Complete time lapse images were obtained. EPSs were able to fuse together, contract, and create a void in fibrin as shown in the FIG. 5A (top right). The void created in fibrin might indicate that the mechanical contraction of fusing EPSs was stronger than the strength of the fibrin hydrogel. Fibrin microstructure allowed migration of RHMVECs, while βTC3 cells maintained their position within the EPSs.

Figures 6A, 6B, 6C:
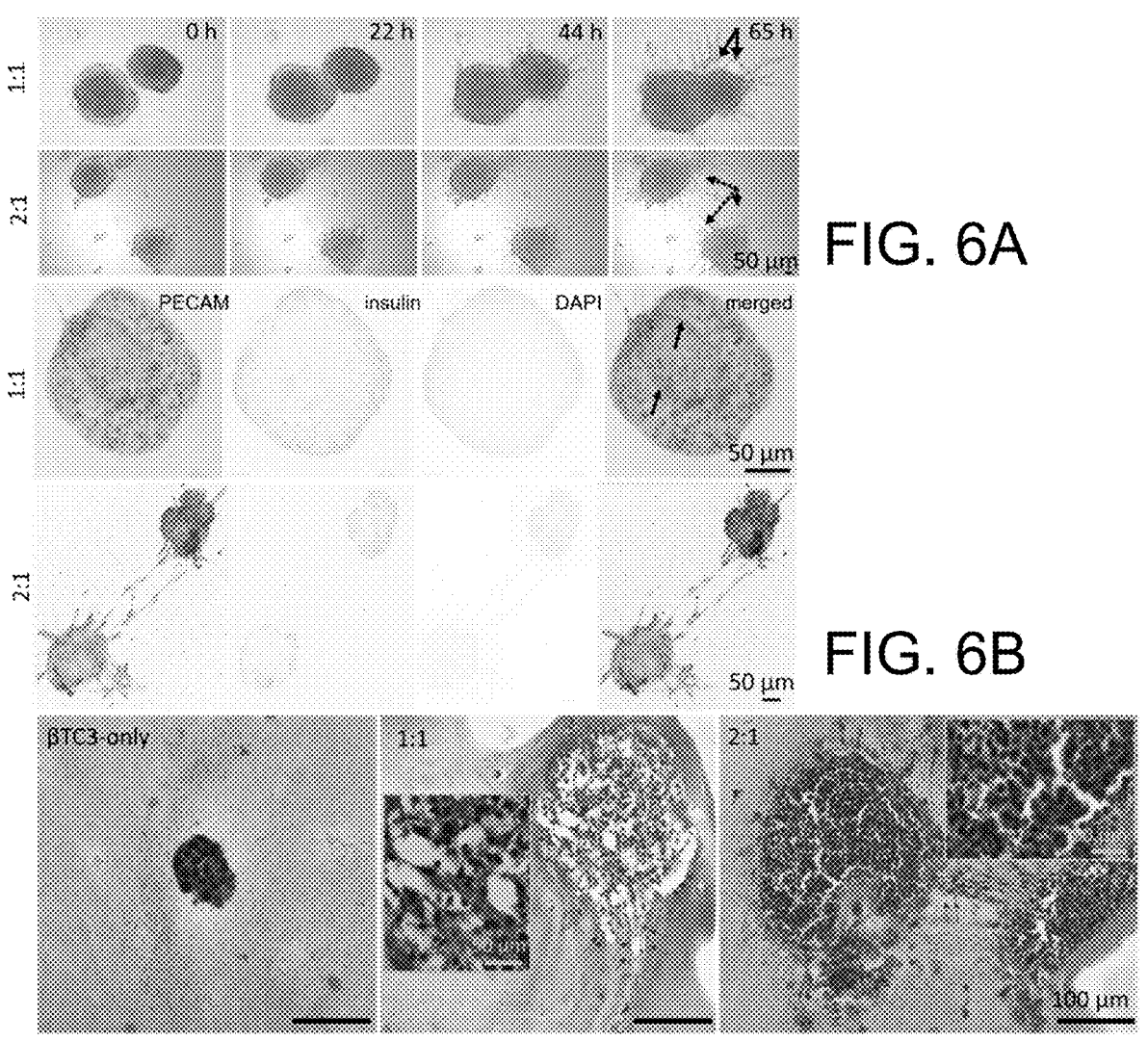
FIG. 6 shows EPSs seeded within the fibrin hydrogel. (A) FIG. 6A contains time laps images of EPSs containing a 1:1 ratio of βTC3 cells to RHMVEC cells (top) or a 2:1 ratio of βTC3 cells to RHMVEC cells (bottom) over a 65-hour period and observed in a live cell imaging chamber. The solid arrows indicate the void space caused by the contraction of EPSs and the dotted arrows demonstrate the endothelial sprouting. (B) FIG. 6B contains microscope images of immunocytochemistry showing endothelial cells sprouting. Vasculature formation in the core of EPSs containing a 1:1 ratio of βTC3 cells to RHMVEC cells (top) or a 2:1 ratio of βTC3 cells to RHMVEC cells (bottom). PECAM (CD31) of shows RHMVEC, insulin shows βTC3, and DAPI shows nuclei. (C) FIG. 6C contains microscope images of H&E staining of EPSs containing βTC3-only (left), a 1:1 ratio of βTC3 cells to RHMVEC cells (middle), or a 2:1 ratio of $TC3 cells to RHMVEC cells (right), cultured for five days in fibrin, and observed at magnification of 20 and 40. (D) FIG. 6D contains bar graphs showing capillary sprouting length (top) and capillary number (bottom) over a period of five days in culture.

Immunocytochemistry was performed on EPSs to understand the sprouting behavior of RHMVEC. RHMVECs exhibited typical endothelial sprouting within the fibrin, while βTC3 cells stained with insulin antibody were maintained within the EPS over the culture period. Endothelial cells also formed vascularization within EPSs after two days in culture (FIG. 6B, top), thicker vessels were formed. When EPSs were placed close together, sprouts between them tended to merge as what appears to be a nascent vascular network (FIG. 6B bottom).

EPSs formed from a 1:1 ratio of βTC3 to RHMVEC and EPSs formed from a 2:1 ratio of βTC3 to RHMVEC underwent histological investigation by H&E staining. The morphology of EPS in both 1:1 and 2:1 ratios showed the duct-like lumens. The 1:1 ratio was characterized by more lose structure with larger voids and vascularization inside the EPS. Contraction of EPS in 1:1 ratio was large and caused a void in fibrin hydrogel, as shown on FIG. 6C (red arrows). In 2:1 group, where were more βTC3 cells than RHMVEC, the morphology was more compact, with smaller gaps. However, the duct-like lumens were present.

Figure 6D:
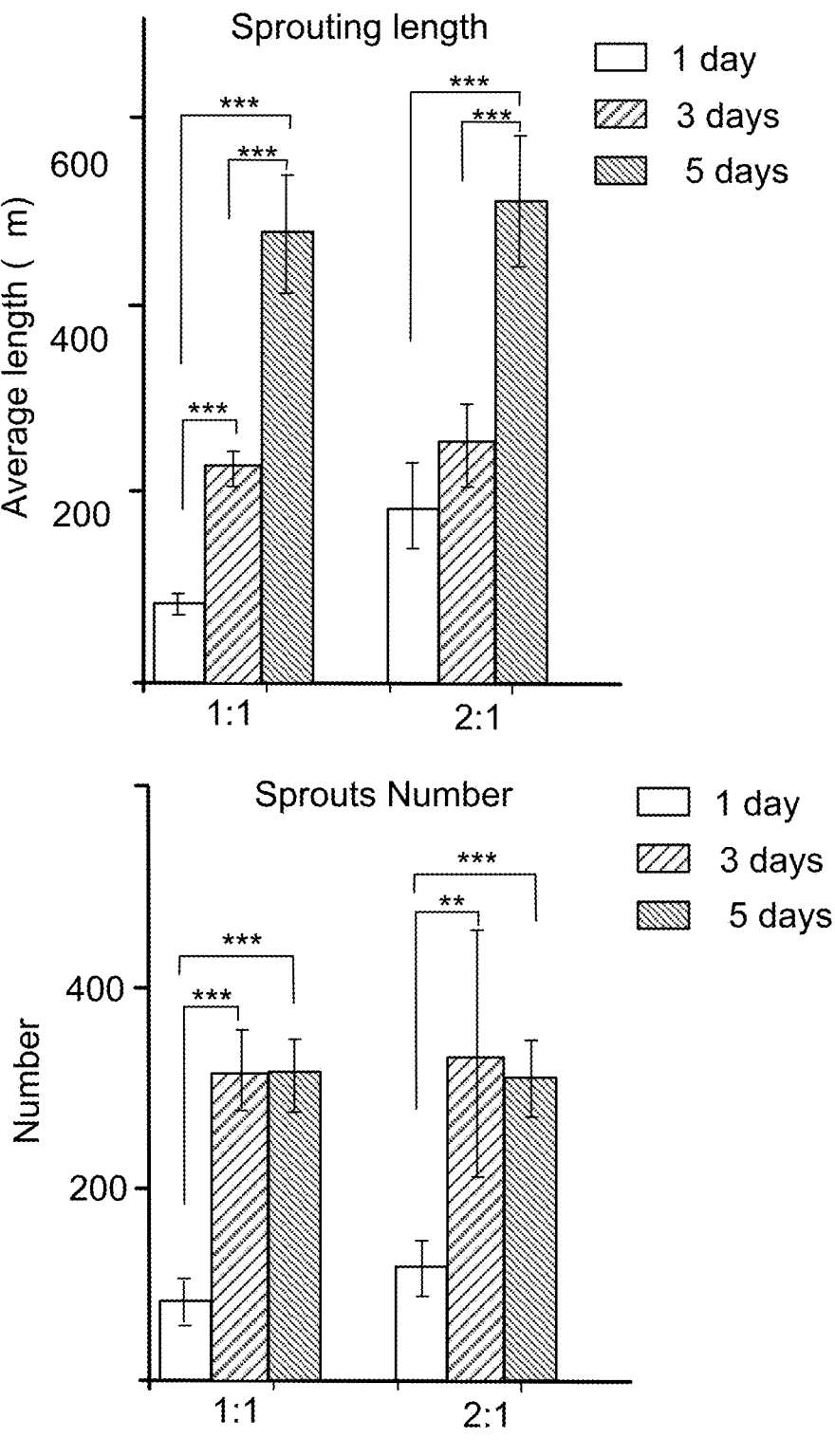

Sprouting length and number was determined in EPSs formed from a 1:1 ratio of βTC3 to RHMVEC and in EPSs formed from a 2:1 ratio of βTC3 to RHMVEC at three time points (1, 3, and 5 days) as shown in the FIG. 6D. The average sprouting length increased by about 65% from $1^{st}$ day to $3^{rd}$ day and by about 83% to $5^{th}$ day of culture for EPSs containing 1:1 ratio of βTC3 to RHMVEC. A similar trend in increase of sprout length was observed for the 2:1 ratio of βTC3 to RHMVEC which underwent an increase of about 28% to 64% over a period of five days. Longer sprouts in case of 2:1 ratio could be attributed to the VEGF production by βTC3 and sturdier nature of the tissue spheroids of a 2:1 ratio of βTC3 to RHMVEC. The number of sprouts increased significantly from $1^{st}$ day to $3^{rd}$ day by 75% but no significant increase was seen from $3^{rd}$ to $5^{th}$ day of culture. This was supported by the fact that as the number of sprouts increased from day 1 to day 3, the growth of new sprouts was hindered by steric crowding of already existing sprouts and was limited by the thickness of the fibrin hydrogel.

Together, these results demonstrate that O-cells cultured in 3D can be vascularized to generated viable and functional clusters (EPSs). Functional EPSs can act as building blocks to form larger, viable tissue constructs for various purposes such as engineering functional organ (e.g., human pancreas) models.

Example 2: Generation of Human Beta (β) Cells

Figure 7A:
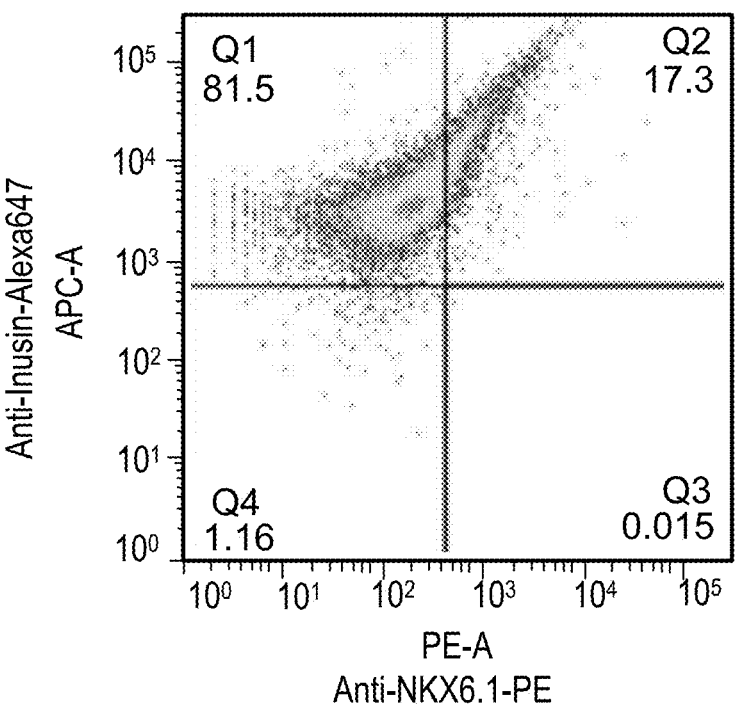
FIG. 7 shows that ADSC-derived β-cells are functional. (A) A flow cytometry dot-plot of ADCS-derived β-cells double stained against insulin and NKX 6.1. (B) A flow cytometry dot-plot of ADCS-derived β-cells double stained against C-peptide and NKX 6.1. (C) A bar graph of insulin release in ADCS-derived β-cells in response to glucose.
Figure 7B:
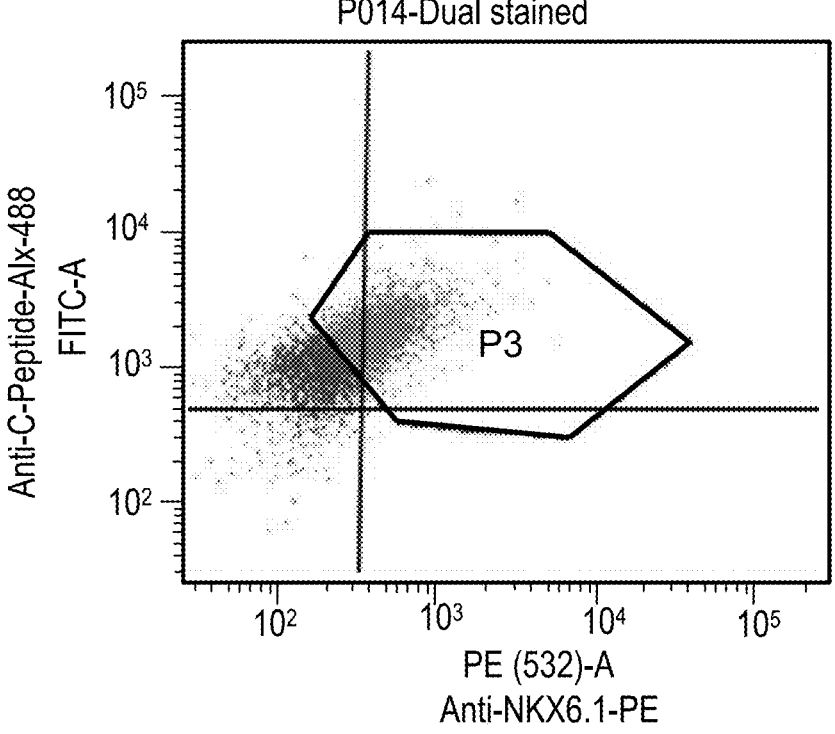
Figure 7C:
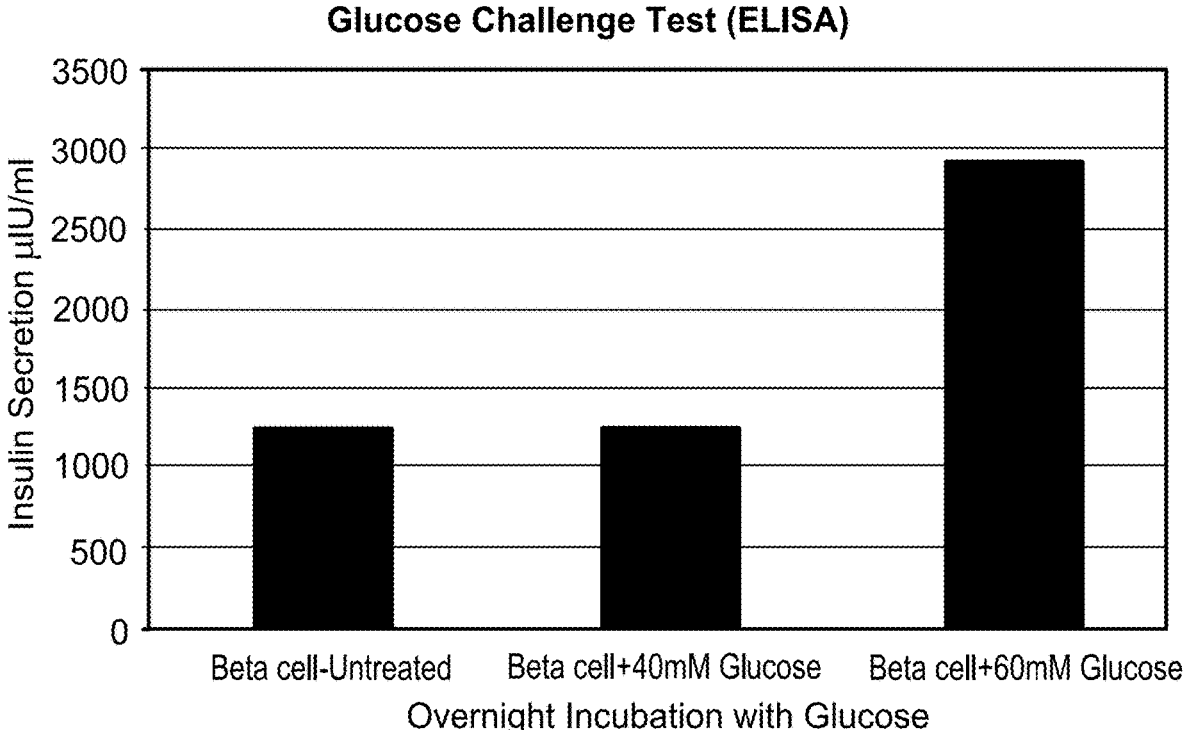

Patients who underwent elective adipose tissue removal (e.g. panniculectomy) consented to have their surgically discarded tissue utilized for pancreatic cell regeneration. Briefly, excised adipose tissue was minced and rinsed to remove residual blood and digested with collagenase at 37° C., and subsequently centrifuged to isolate the stromal vascular fraction (SVF) pellet. The SVF was further washed in buffer and underwent magnetic activated cell sorting (MACS) with CD45+ cells (leukocytes) being extracted and discarded. The leukocyte depleted SVF fraction underwent two rounds of MACS isolation of ECs (CD31) and pericytes (CD146 and NG2). The remaining depleted SVF fraction consisted primarily of adipocyte-derived stem cells (AD-SCs) (CD73+ and CD90+). Cellular isolates were verified by flow cytometry for yield and purity. Microvascular endothelial cells (MVECs) and pericytes were maintained and expanded in appropriate maintenance media and conditions. Aliquotted ADSCs (500,000 per well) underwent directed in vitro differentiation to β-cells, over a 30-day period in 3 media formulations: Media 1 (DMEM/F-12, 30% FBS, 1% N-2 supplement) for 10 days, Media 2 (DMEM/F-12, 2% FBS, 1% N-2, 2% B-27, b-FGF, 10 mM Nicotinamide) for 10 days, and Media 3 (DMEM/F-12, 1% N-2, 2% B-27 serum free supplement, β-FGF, 10 mM Nicotinamide, 1 mM sodium pyruvate, 1× ITS (insulin, transferrin, selenium supplement)) for the final 10 days. Differentiated β-cells were characterized and sorted using flow cytometry (FIGS. 7 A-B) showing their functionality while validating their glucose responsiveness (FIG. 7C).

These results demonstrate that functional human β-cells can be generated from human adipose tissue (e.g., ADSC-derived β-cells).

Example 3: Bioprinting a Perfusable
Pancreas-On-a-Chip Model

Figures 9A, 9B:
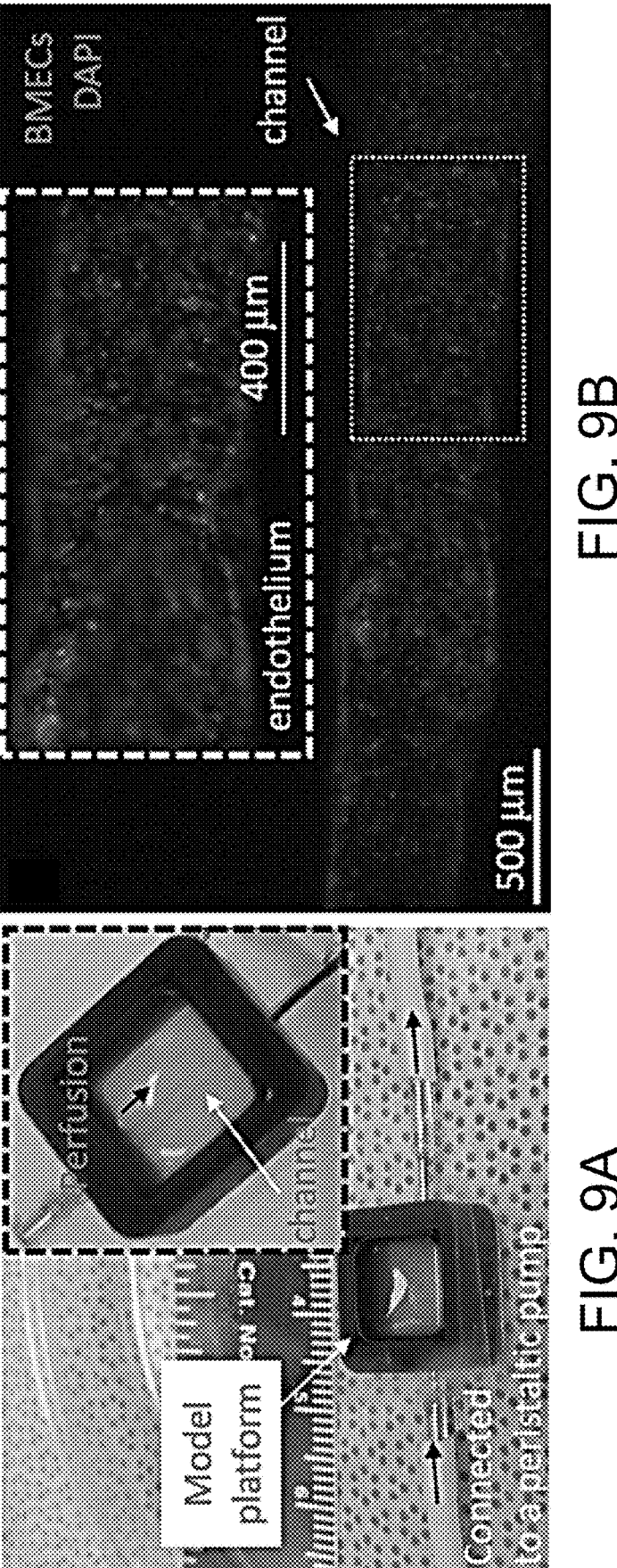
FIG. 9 contains a schematic showing bioprinting of an exemplary perfusable pancreas-on-a-chip model. (A) The perfusable model platform (B) lined up with a single-layer of bone marrow endothelial cells (BMECs) under the proposed perfusion settings. (C) Encapsulated islets in fibrin sprouted robust capillaries in 2 weeks. (D1) Sprouted capillaries allowed intravasation of MDA-MB-231 metastatic cancer cells when they were seeded originally within the cell aggregates. (D2) Capillaries also sprouted from tumor spheroids made of breast cancer cells (MDA-MB-231), human umbilical vascular endothelial cells (HUVECs), and fibroblasts. (E1) Bioprinting of islets in a circular pattern using a new aspiration-assisted bioprinting process. (E2) Bioprinting of islets of pancreas of tumor spheroids in a pattern spelling PSU, standing for Penn State University, using a new aspiration-assisted bioprinting process.

A hybrid bioprinting technology was developed to build a pancreas-on-a-chip model using fabricated pre-vascularized islets. A two-part device was used where a cover slide was attached to the bottom face of the device for imaging purposes. The detailed steps undertaken are as shown in FIG. 8 (see, e.g., Steps 1-6). After building the platform (see, e.g., FIG. 9A), MVECs were seeded into the channel to allow them to settle and attach on both sides of the channels (see, e.g., FIG. 8, Step 7).

Figure 9C:
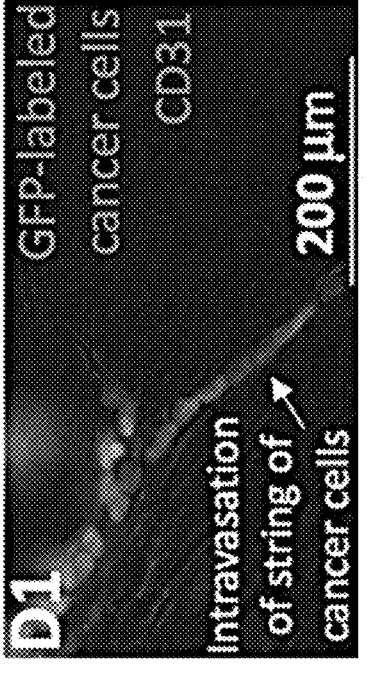
Figure 9C:
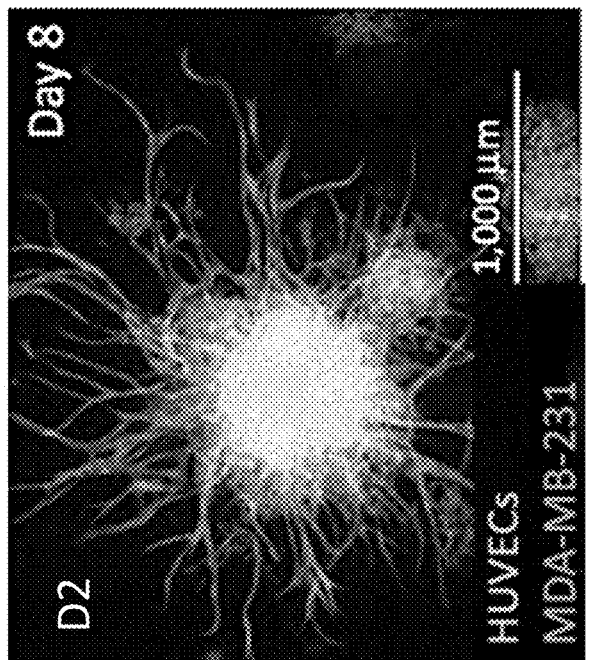
Figure 9C:
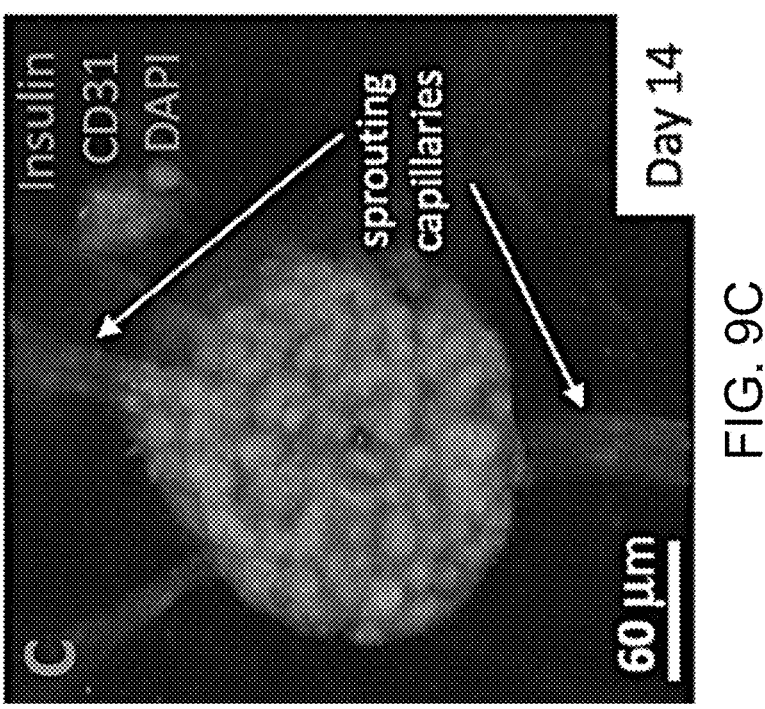

After seeding MVECs, the device was perfused. To train MVECs to better attach and make tight junctions in 3 days, the device was perfused with a shear rate of 0.1 dyne/cm$^2$ during the first 6 hours, 1 dyne/cm$^2$ thereafter during the first day, followed by 10 dyne/cm$^2$ after the first day (see, e.g., FIG. 9B). The device was perfused for 14 days. Around Days 5-7, capillary formation in the gel and robust capillary sprouts from islets was obtained (see, e.g., FIG. 8, Step 8), followed by sprouting of capillaries from the main channel and anastomosis of these capillaries with the capillaries growing in the gel around Days 10-12 (FIG. 8, Step 9, and FIG. 9C, D1, and D2).

In order to bioprint pancreatic islets, a custom-made bioprinter was developed. The bioprinter, which runs using the aspiration principle, enables bioprinting of pancreatic islets (or any other organoids) that is more precise and more accurate than is achievable by manual deposition.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making a pancreas model, said method comprising:
   disposing a first layer of extracellular matrix onto a substrate assembled into a model platform;
   disposing a strand of sacrificial matrix onto an interior region of said first layer of extracellular matrix;
   using an aspiration-assisted bioprinting process to bioprint an array of engineered pancreatic islets comprising pre-vascularized pancreatic spheroids onto said first layer of extracellular matrix;
   disposing a second layer of extracellular matrix onto said array of pancreatic islets;
   removing said sacrificial matrix with an aspiration removal process to create a channel;
   seeding said channel with microvessel endothelial cells; and
   perfusing said channel with perfusate,
   wherein said pancreas model comprises from about 20 islets to about 50 islets per mm$^3$ of said pancreas model, and
   wherein said pancreas model comprises a vascular network comprising microvascularization within pancreatic islets.

2. The method of claim 1, wherein disposing said first layer of extracellular matrix comprises alternately disposing a first layer comprising thrombin, endothelial cells (ECs), pericytes, and CaCl$_2$, and disposing a second layer comprising fibrinogen on said first layer.

3. The method of claim 1, wherein said sacrificial matrix is selected from the group consisting of alginate, agarose, gelatin, sugar, and poloxamer.

4. The method of claim 1, wherein said pre-vascularized pancreatic spheroids are engineered by co-culturing beta cells and microvessel endothelial cells.

5. The method of claim 1, wherein disposing said second layer of extracellular matrix comprises alternately disposing a first layer comprising thrombin, ECs, pericytes, and CaCl$_2$, and disposing a second layer comprising fibrinogen on said first layer until said model platform is full.

6. The method of claim 1, wherein said sacrificial matrix comprises alginate.

7. The method of claim 1, wherein said channel is perfused with laminar flow.

8. The method of claim 1, wherein said channel is perfused for a total of 14 days starting with a rate of about 0.1 dyne/cm$^2$ for about 6 hours, followed by a rate of about 1 dyne/cm$^2$ for about 18 hours, followed by a rate of about 10 dyne/cm$^2$ for about 13 days.

9. The method of claim 1, where said pancreas model is a patient-specific pancreas model.

10. The method of claim 1, wherein disposing the first and second layers of extracellular matrix comprises alternately depositing said first and second layers using a layer-by-layer bioprinting process.

11. A method of making a pancreas model, said method comprising:
   disposing a first layer of extracellular matrix onto a substrate assembled into a model platform;
   disposing a strand of sacrificial matrix onto an interior region of said first layer of extracellular matrix;
   disposing an array of engineered pancreatic islets comprising pre-vascularized pancreatic spheroids onto said first layer of extracellular matrix;
   disposing a second layer of extracellular matrix onto said array of pancreatic islets;
   removing said sacrificial matrix with a solution to create a channel;
   seeding said channel with microvessel endothelial cells; and
   perfusing said channel with perfusate,
   wherein said pre-vascularized pancreatic spheroids are engineered, prior to disposing said first layer of extracellular matrix onto said substrate, by co-culturing beta cells and microvessel endothelial cells,
   wherein said beta cells and said microvessel endothelial cells are co-cultured in a ratio of from about 1:1 to about 10:1,
   wherein said pancreas model comprises from about 20 islets to about 50 islets per mm$^3$ of said pancreas model, and
   wherein said pancreas model comprises a vascular network comprising microvascularization within pancreatic islets.

12. The method of claim 11, wherein disposing said first layer of extracellular matrix comprises alternately disposing a first layer comprising thrombin, endothelial cells (ECs), pericytes, and CaCl$_2$, and disposing a second layer comprising fibrinogen on said first layer.

13. The method of claim 11, wherein said sacrificial matrix is selected from the group consisting of alginate, agarose, gelatin, sugar, and poloxamer.

14. The method of claim 11, wherein said beta cells are selected from the group consisting of adipose-derived stem cell derived beta cells, pluripotent stem cell derived beta cells, fibroblast derived beta cells, and combinations thereof.

15. The method of claim 11, wherein said beta cells and said microvessel endothelial cells are co-cultured in the presence of a growth factor.

16. The method of claim 15, wherein said growth factor is selected from the group consisting of vascular endothelial growth factor, epidermal growth factor, and fibroblast growth factor.

17. The method of claim 11, wherein disposing said second layer of extracellular matrix comprises alternately disposing a first layer comprising thrombin, ECs, pericytes, and $CaCl_2$, and disposing a second layer comprising fibrinogen on said first layer until said model platform is full.

18. The method of claim 11, wherein said solution comprises sodium citrate.

19. The method of claim 11, wherein said channel is perfused with laminar flow.

20. The method of claim 11, wherein said channel is perfused for a total of 14 days starting with a rate of about 0.1 dyne/$cm^2$ for about 6 hours, followed by a rate of about 1 dyne/$cm^2$ for about 18 hours, followed by a rate of about 10 dyne/$cm^2$ for about 13 days.

* * * * *